US009259149B2

(12) United States Patent
Holladay et al.

(10) Patent No.: US 9,259,149 B2
(45) Date of Patent: *Feb. 16, 2016

(54) OPHTHALMIC SURGERY MEASUREMENT SYSTEM

(71) Applicant: WaveTec Vision Systems, Inc., Aliso Viejo, CA (US)

(72) Inventors: Jack T. Holladay, Bellaire, TX (US);
Thomas D. Padrick, Seattle, WA (US);
Richard J. Michaels, Irvine, CA (US)

(73) Assignee: WaveTec Vision Systems, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/039,965

(22) Filed: Sep. 27, 2013

(65) Prior Publication Data
US 2014/0132931 A1 May 15, 2014

Related U.S. Application Data

(63) Continuation of application No. 12/835,665, filed on Jul. 13, 2010, now Pat. No. 8,545,023.

(60) Provisional application No. 61/225,547, filed on Jul. 14, 2009.

(51) Int. Cl.
*A61B 3/14* (2006.01)
*A61B 3/00* (2006.01)
(Continued)

(52) U.S. Cl.
CPC ............... *A61B 3/1005* (2013.01); *A61F 2/16* (2013.01); *A61F 2240/002* (2013.01)

(58) Field of Classification Search
USPC .......................... 351/206, 208, 210, 221, 246
See application file for complete search history.

(56) References Cited

U.S. PATENT DOCUMENTS 3,947,186 A 3/1976 Howland
4,019,813 A 4/1977 Cornsweet et al.
(Continued)

FOREIGN PATENT DOCUMENTS

AU 2005234778 8/2011
CA 2521845 11/2004
(Continued)

OTHER PUBLICATIONS

Combined International Search Report and Written Opinion of the International Searching Authority for International Application No. PCT/US05/13550; issued by the ISA/US; dated Nov. 15. 2005.
(Continued)

*Primary Examiner* — Jack Dinh
(74) *Attorney, Agent, or Firm* — Baker Botts L.L.P.

(57) ABSTRACT

An ophthalmic apparatus for measuring spatial distances within a patient's eye is disclosed. The apparatus can be used to measure, for example, the capsular bag depth in an aphakic eye. The spatial measurement system can direct laser light into a patient's eye so that a portion of the light is scattered by the capsular bag. The scattered light can be directed to a detector where spots can be formed corresponding to the locations on the capsular bag from which the light was scattered. The distance from the cornea to the capsular bag can be determined based, for example, at least in part on the distance between the spots formed on the detector. In some embodiments, the apparatus can include a surgical microscope and/or a wavefront aberrometer. In some embodiments, an alignment system can be used to precisely position the apparatus relative to the patient's eye. The ophthalmic apparatus can be used for variety of ophthalmic procedures, such as predicting the postoperative position of an intraocular lens (IOL) and determining appropriate optical power for the IOL.

24 Claims, 11 Drawing Sheets

(51) Int. Cl.
*A61B 3/10* (2006.01)
*A61F 2/16* (2006.01)

(56) References Cited

U.S. PATENT DOCUMENTS

| | | |
|---|---|---|
| 4,125,320 A | 11/1978 | Rassow |
| 4,172,662 A | 10/1979 | Vogel |
| 4,173,398 A | 11/1979 | Okamoto et al. |
| 4,293,198 A | 10/1981 | Kohayakawa et al. |
| 4,353,625 A | 10/1982 | Nohda et al. |
| 4,372,655 A | 2/1983 | Matsumura et al. |
| 4,376,573 A | 3/1983 | Matsumura et al. |
| 4,390,255 A | 6/1983 | Nohda et al. |
| 4,421,391 A | 12/1983 | Matsumura et al. |
| 4,459,027 A | 7/1984 | Kafri et al. |
| 4,541,697 A | 9/1985 | Ramijan |
| 4,640,596 A | 2/1987 | Humphrey |
| 4,650,301 A | 3/1987 | Humphrey |
| 4,669,835 A | 6/1987 | Humphrey |
| 4,692,003 A | 9/1987 | Adachi et al. |
| 4,710,193 A | 12/1987 | Volk |
| 4,721,379 A | 1/1988 | L'Esperance |
| 4,730,917 A | 3/1988 | Krueger |
| 4,911,711 A | 3/1990 | Telfair et al. |
| 4,964,715 A | 10/1990 | Richards |
| 4,984,883 A | 1/1991 | Winocur |
| 4,995,716 A | 2/1991 | Warnicki et al. |
| 5,080,477 A | 1/1992 | Adachi |
| 5,144,478 A | 9/1992 | Toshimitsu |
| 5,157,427 A | 10/1992 | Humphrey |
| 5,164,750 A | 11/1992 | Adachi |
| 5,202,708 A | 4/1993 | Sasaki et al. |
| 5,206,672 A | 4/1993 | Rowe |
| 5,208,619 A | 5/1993 | Campbell |
| 5,223,863 A | 6/1993 | Heine |
| 5,252,999 A | 10/1993 | Sukigara |
| 5,258,791 A | 11/1993 | Penny et al. |
| 5,270,749 A | 12/1993 | Okamura |
| 5,282,852 A | 2/1994 | Capetan et al. |
| 5,294,971 A | 3/1994 | Braunecker et al. |
| 5,307,097 A | 4/1994 | Baker |
| 5,329,322 A | 7/1994 | Yancey |
| 5,374,193 A | 12/1994 | Trachtman |
| 5,450,143 A | 9/1995 | Rowe et al. |
| 5,455,645 A | 10/1995 | Berger et al. |
| 5,493,109 A | 2/1996 | Wei et al. |
| 5,576,780 A | 11/1996 | Yancey |
| 5,777,719 A | 7/1998 | Williams et al. |
| 5,796,463 A | 8/1998 | Bullimore |
| 5,800,533 A | 9/1998 | Eggleston et al. |
| 5,841,511 A | 11/1998 | D'Souza et al. |
| 5,861,937 A | 1/1999 | Fujieda |
| 5,909,268 A | 6/1999 | Isogai et al. |
| 5,936,706 A | 8/1999 | Takagi |
| 5,949,521 A | 9/1999 | Williams et al. |
| 5,963,300 A | 10/1999 | Horwitz |
| 5,968,094 A | 10/1999 | Werblin et al. |
| 5,968,095 A | 10/1999 | Norrby |
| 5,994,687 A | 11/1999 | Chanteloup et al. |
| 6,002,484 A | 12/1999 | Rozema et al. |
| 6,004,313 A | 12/1999 | Shimmick et al. |
| 6,007,204 A | 12/1999 | Fahrenkrug et al. |
| 6,042,232 A | 3/2000 | Luce et al. |
| 6,043,885 A | 3/2000 | Mazuet et al. |
| 6,050,687 A | 4/2000 | Bille et al. |
| 6,086,204 A | 7/2000 | Magnante |
| 6,095,651 A | 8/2000 | Williams et al. |
| 6,096,077 A | 8/2000 | Callahan et al. |
| 6,155,684 A | 12/2000 | Bille et al. |
| 6,199,986 B1 | 3/2001 | Williams et al. |
| 6,251,101 B1 | 6/2001 | Glockler |
| 6,262,328 B1 | 7/2001 | Wicks et al. |
| 6,264,328 B1 | 7/2001 | Williams et al. |
| 6,270,221 B1 | 8/2001 | Liang et al. |
| 6,271,915 B1 | 8/2001 | Frey et al. |
| 6,275,718 B1 | 8/2001 | Lempert |
| 6,299,311 B1 | 10/2001 | Williams et al. |
| 6,299,618 B1 | 10/2001 | Sugiura |
| 6,338,559 B1 | 1/2002 | Williams et al. |
| 6,379,005 B1 | 4/2002 | Williams et al. |
| 6,382,793 B1 | 5/2002 | Lai et al. |
| 6,382,794 B1 | 5/2002 | Lai et al. |
| 6,382,795 B1 | 5/2002 | Lai |
| 6,394,605 B1 | 5/2002 | Campin et al. |
| 6,409,345 B1 | 6/2002 | Molebny et al. |
| 6,419,671 B1 | 7/2002 | Lemberg |
| 6,439,720 B1 | 8/2002 | Graves et al. |
| 6,460,997 B1 | 10/2002 | Frey et al. |
| 6,497,483 B2 | 12/2002 | Frey et al. |
| 6,508,812 B1 | 1/2003 | Williams et al. |
| 6,511,180 B2 | 1/2003 | Guirao et al. |
| 6,550,917 B1 | 4/2003 | Neal et al. |
| 6,561,648 B2 | 5/2003 | Thomas |
| 6,570,143 B1 | 5/2003 | Neil et al. |
| 6,572,230 B2 | 6/2003 | Levine |
| 6,575,572 B2 | 6/2003 | Lai et al. |
| 6,578,963 B2 | 6/2003 | Pettit |
| 6,585,723 B1 | 7/2003 | Sumiya |
| 6,588,902 B2 | 7/2003 | Isogai |
| 6,598,975 B2 | 7/2003 | Liang et al. |
| 6,601,956 B1 | 8/2003 | Jean et al. |
| 6,609,793 B2 | 8/2003 | Norrby et al. |
| 6,609,794 B2 | 8/2003 | Levine |
| 6,626,535 B2 | 9/2003 | Altmann |
| 6,626,538 B1 | 9/2003 | Arrowsmith |
| 6,634,751 B2 | 10/2003 | Turner et al. |
| 6,637,884 B2 | 10/2003 | Martino |
| 6,658,282 B1 | 12/2003 | Eagan et al. |
| 6,679,606 B2 | 1/2004 | Campin et al. |
| 6,685,319 B2 | 2/2004 | Watson et al. |
| 6,702,806 B2 | 3/2004 | Gray et al. |
| 6,705,729 B2 | 3/2004 | Piers et al. |
| 6,724,464 B2 | 4/2004 | Yang et al. |
| 6,736,509 B2 | 5/2004 | Martino et al. |
| 6,736,510 B1 | 5/2004 | Van Heugten |
| 6,739,721 B2 | 5/2004 | Altmann |
| 6,761,454 B2 | 7/2004 | Lai et al. |
| 6,781,681 B2 | 8/2004 | Horwitz |
| 6,786,603 B2 | 9/2004 | Altmann |
| 6,793,654 B2 | 9/2004 | Lemberg |
| 6,819,413 B2 | 11/2004 | Neal et al. |
| 6,827,444 B2 | 12/2004 | Williams et al. |
| 6,836,374 B2 | 12/2004 | Esch et al. |
| 6,905,641 B2 | 6/2005 | Platt et al. |
| 6,908,196 B2 | 6/2005 | Herekar et al. |
| 6,926,710 B2 | 8/2005 | Cox et al. |
| 6,948,818 B2 | 9/2005 | Williams et al. |
| 6,997,555 B2 | 2/2006 | Dick et al. |
| 7,018,376 B2 | 3/2006 | Webb |
| 7,034,949 B2 | 4/2006 | Horwitz |
| 7,044,602 B2 | 5/2006 | Chernyak |
| 7,044,604 B1 | 5/2006 | Arrowsmith |
| 7,057,806 B2 | 6/2006 | Atkinson |
| 7,066,928 B2 | 6/2006 | Dick et al. |
| 7,068,439 B2 | 6/2006 | Esch et al. |
| 7,070,276 B2 | 7/2006 | Koretz |
| 7,077,522 B2 | 7/2006 | Williams |
| 7,111,938 B2 | 9/2006 | Andino et al. |
| 7,182,780 B2 | 2/2007 | Terwee et al. |
| 7,237,898 B1 | 7/2007 | Hohla et al. |
| 7,255,442 B2 | 8/2007 | Bucourt et al. |
| 7,303,281 B2 | 12/2007 | Wakil et al. |
| 7,336,371 B1 | 2/2008 | Haidner et al. |
| 7,341,348 B2 | 3/2008 | Eagan |
| 7,350,916 B2 | 4/2008 | Hong et al. |
| 7,350,920 B2 | 4/2008 | Levine |
| 7,357,509 B2 | 4/2008 | Williams et al. |
| 7,374,286 B2 | 5/2008 | Fujieda et al. |
| 7,377,641 B2 | 5/2008 | Piers et al. |
| 7,380,942 B2 | 6/2008 | Molebny et al. |
| 7,401,919 B2 | 7/2008 | Vogelsang et al. |
| 7,406,263 B2 | 7/2008 | Graves et al. |
| 7,416,305 B2 | 8/2008 | Williams et al. |
| 7,425,067 B2 | 9/2008 | Warden et al. |

(56) References Cited

U.S. PATENT DOCUMENTS

| | | | |
|---|---|---|---|
| 7,441,901 B2 | 10/2008 | Liang |
| 7,445,335 B2 | 11/2008 | Su et al. |
| 7,448,752 B2 | 11/2008 | Levine |
| 7,455,407 B2 | 11/2008 | Neal et al. |
| 7,461,938 B2 | 12/2008 | Lai |
| 7,467,869 B2 | 12/2008 | Kahlen |
| 7,475,989 B2 | 1/2009 | Campbell et al. |
| 7,476,248 B2 | 1/2009 | Harris et al. |
| 7,478,908 B2 | 1/2009 | Lai et al. |
| 7,490,938 B2 | 2/2009 | Latkany |
| 7,490,940 B2 | 2/2009 | Lai et al. |
| 7,517,087 B2 | 4/2009 | Dick et al. |
| 7,543,937 B2 | 6/2009 | Piers et al. |
| 7,556,378 B1 | 7/2009 | Ianchulev |
| 7,594,729 B2 | 9/2009 | Van Heugten |
| 7,845,798 B2 | 12/2010 | Kuebler |
| 7,850,308 B2 | 12/2010 | Rombach |
| 7,878,655 B2 | 2/2011 | Salvati et al. |
| 7,883,505 B2 | 2/2011 | Van Heugten et al. |
| 7,887,184 B2 | 2/2011 | Baer et al. |
| 7,988,291 B2 | 8/2011 | Ianchulev |
| 8,002,410 B2 | 8/2011 | Shea |
| 8,313,196 B2 | 11/2012 | Ianchulev |
| 8,333,474 B2 | 12/2012 | Michaels et al. |
| 8,394,083 B2 | 3/2013 | Van Heugten et al. |
| 8,480,659 B2 | 7/2013 | Frey et al. |
| 8,545,023 B2 * | 10/2013 | Holladay et al. ............ 351/221 |
| 8,550,624 B2 | 10/2013 | Padrick et al. |
| 8,619,405 B2 | 12/2013 | Van Heugten |
| 8,632,185 B2 | 1/2014 | Ianchulev |
| 8,876,290 B2 | 11/2014 | Sarver et al. |
| 2001/0041884 A1 | 11/2001 | Frey et al. |
| 2002/0016629 A1 | 2/2002 | Sandstedt et al. |
| 2002/0082629 A1 | 6/2002 | Cox et al. |
| 2002/0105617 A1 | 8/2002 | Norrby et al. |
| 2002/0107567 A1 | 8/2002 | Terwee et al. |
| 2002/0118349 A1 | 8/2002 | Yang et al. |
| 2002/0133228 A1 | 9/2002 | Sarver |
| 2002/0135736 A1 | 9/2002 | Stark et al. |
| 2002/0154272 A1 | 10/2002 | Shevlin |
| 2002/0158508 A1 | 10/2002 | Watanabe |
| 2002/0163623 A1 | 11/2002 | Hirohara et al. |
| 2003/0007125 A1 | 1/2003 | Levine |
| 2003/0007127 A1 | 1/2003 | Levine |
| 2003/0009156 A1 | 1/2003 | Levine |
| 2003/0025080 A1 | 2/2003 | Sting et al. |
| 2003/0053025 A1 | 3/2003 | Turner et al. |
| 2003/0139736 A1 | 7/2003 | Sander |
| 2003/0174281 A1 | 9/2003 | Herekar et al. |
| 2003/0223037 A1 | 12/2003 | Chernyak |
| 2003/0230710 A1 | 12/2003 | Wolleschensky et al. |
| 2004/0010310 A1 | 1/2004 | Peyman |
| 2004/0054358 A1 | 3/2004 | Cox et al. |
| 2004/0088050 A1 | 5/2004 | Norrby et al. |
| 2004/0156014 A1 | 8/2004 | Piers et al. |
| 2004/0167622 A1 | 8/2004 | Sunalp et al. |
| 2004/0176753 A1 | 9/2004 | Dick et al. |
| 2004/0189938 A1 | 9/2004 | Eagan |
| 2004/0223214 A1 | 11/2004 | Atkinson |
| 2004/0263785 A1 | 12/2004 | Chernyak |
| 2005/0007603 A1 | 1/2005 | Arieli |
| 2005/0068497 A1 | 3/2005 | Hanebuchi et al. |
| 2005/0105044 A1 | 5/2005 | Warden et al. |
| 2005/0110949 A1 | 5/2005 | Goldfain et al. |
| 2005/0117117 A1 | 6/2005 | Bourla |
| 2005/0195360 A1 | 9/2005 | Akita et al. |
| 2005/0203422 A1 | 9/2005 | Wei |
| 2005/0225725 A1 | 10/2005 | Warden et al. |
| 2005/0241653 A1 | 11/2005 | Van Heugten |
| 2005/0243276 A1 | 11/2005 | Van Heugten et al. |
| 2005/0251115 A1 | 11/2005 | Cox et al. |
| 2005/0278004 A1 | 12/2005 | Steinert et al. |
| 2006/0007395 A1 | 1/2006 | Mayo et al. |
| 2006/0007397 A1 | 1/2006 | Lai |
| 2006/0084956 A1 | 4/2006 | Sumiya |
| 2006/0126018 A1 | 6/2006 | Liang |
| 2006/0126019 A1 | 6/2006 | Liang et al. |
| 2006/0135952 A1 | 6/2006 | Curatu et al. |
| 2006/0174281 A1 | 8/2006 | Park |
| 2006/0203196 A1 | 9/2006 | Van Heugten |
| 2006/0203198 A1 | 9/2006 | Liang |
| 2006/0232744 A1 | 10/2006 | Liang |
| 2006/0247659 A1 | 11/2006 | Moeller et al. |
| 2006/0279699 A1 | 12/2006 | Liang |
| 2007/0024808 A1 | 2/2007 | Campin et al. |
| 2007/0027442 A1 | 2/2007 | Campin et al. |
| 2007/0070292 A1 | 3/2007 | Liang |
| 2007/0070293 A1 | 3/2007 | Isogai |
| 2007/0115432 A1 | 5/2007 | Thibos |
| 2007/0236702 A1 | 10/2007 | Neal et al. |
| 2007/0260157 A1 | 11/2007 | Norrby |
| 2008/0004610 A1 | 1/2008 | Miller et al. |
| 2008/0033546 A1 | 2/2008 | Liang |
| 2008/0084541 A1 | 4/2008 | Lai et al. |
| 2008/0088795 A1 | 4/2008 | Goldstein et al. |
| 2008/0159642 A1 | 7/2008 | Lyuboshenko |
| 2008/0231809 A1 | 9/2008 | Haigis |
| 2008/0278683 A1 | 11/2008 | Su et al. |
| 2008/0281304 A1 | 11/2008 | Campbell |
| 2008/0291396 A1 | 11/2008 | Baer et al. |
| 2009/0002628 A1 | 1/2009 | Williams et al. |
| 2009/0002631 A1 | 1/2009 | Campbell et al. |
| 2009/0009717 A1 | 1/2009 | Barrett et al. |
| 2009/0036980 A1 | 2/2009 | Norrby et al. |
| 2009/0048608 A1 | 2/2009 | Boukhny et al. |
| 2009/0096987 A1 | 4/2009 | Lai et al. |
| 2009/0103050 A1 | 4/2009 | Michaels et al. |
| 2009/0109401 A1 | 4/2009 | Van Heugten |
| 2009/0164007 A1 | 6/2009 | Van Heugten |
| 2010/0030225 A1 | 2/2010 | Ianchulev |
| 2010/0042210 A1 | 2/2010 | Ianchulev |
| 2011/0001960 A1 | 1/2011 | Van Heugten |
| 2011/0013141 A1 | 1/2011 | Holladay et al. |
| 2011/0015541 A1 | 1/2011 | Padrick |
| 2011/0242482 A1 | 10/2011 | Olsen |
| 2011/0267579 A1 | 11/2011 | Van Heugten |
| 2012/0147460 A1 | 6/2012 | Kubler |
| 2013/0021574 A1 | 1/2013 | Van Heugten |
| 2013/0070203 A1 | 3/2013 | Michaels |
| 2013/0335705 A1 | 12/2013 | Heugten |
| 2014/0085604 A1 | 3/2014 | Michaels |
| 2014/0111772 A1 | 4/2014 | Ikegami |
| 2014/0132922 A1 | 5/2014 | Padrick |
| 2014/0249624 A1 | 9/2014 | Ianchulev |
| 2014/0313487 A1 | 10/2014 | Heugten |
| 2015/0092158 A1 | 4/2015 | Padrick et al. |
| 2015/0157200 A1 | 6/2015 | Sarver |

FOREIGN PATENT DOCUMENTS

| | | |
|---|---|---|
| CA | 2515010 | 5/2013 |
| CN | 2010-80040737.6 | 6/2011 |
| CN | 102497833 A | 6/2012 |
| DE | 43 10 561 A1 | 9/1994 |
| DE | 19 85 7001 A1 | 6/2000 |
| EP | 0931504 A1 | 7/1999 |
| EP | 2444021 | 4/2012 |
| EP | 2453822 | 5/2012 |
| EP | 2453823 | 5/2012 |
| EP | 1596710 | 1/2013 |
| EP | 1 737 372 | 8/2014 |
| EP | 2 818 130 | 12/2014 |
| EP | 2 453 823 | 5/2015 |
| GB | 1 209 451 | 10/1970 |
| IL | 138282 | 7/2004 |
| JP | 11-24434 | 5/1989 |
| JP | 9-122075 | 5/1997 |
| JP | 10-272100 | 10/1998 |
| JP | 2000-139996 | 5/2000 |
| JP | 2000-197607 | 7/2000 |
| JP | 2001-507258 A | 6/2001 |
| JP | 2001-314372 A | 11/2001 |
| JP | 2002-306418 A | 10/2002 |
| JP | 2003-509731 A | 3/2003 |

(56) References Cited

FOREIGN PATENT DOCUMENTS

| | | |
|---|---|---|
| JP | 2003-102689 A | 4/2003 |
| JP | 4972546 | 4/2003 |
| WO | WO 92/01417 | 2/1992 |
| WO | WO 96/22506 | 7/1996 |
| WO | WO 98/27863 | 7/1998 |
| WO | WO 01/06914 | 2/2001 |
| WO | WO 01/21061 A1 | 3/2001 |
| WO | WO 01/26591 A1 | 4/2001 |
| WO | WO 01/58339 | 8/2001 |
| WO | WO 02/17775 | 3/2002 |
| WO | WO 03/002047 | 1/2003 |
| WO | WO 03/039356 | 5/2003 |
| WO | WO 03/050472 A1 | 6/2003 |
| WO | WO 03/102498 A1 | 12/2003 |
| WO | WO 2004/093663 A2 | 11/2004 |
| WO | WO 2005/057252 | 6/2005 |
| WO | WO 2006/081031 A2 | 8/2006 |
| WO | WO 2009/086059 | 7/2009 |
| WO | WO 14/052479 | 4/2014 |

OTHER PUBLICATIONS

Restriction Requirement issued on Apr. 10, 2007 in U.S. Appl. No. 10/820,635, filed Apr. 8, 2004.
Non-Final Office Action issued on Jul. 11, 2007 in U.S. Appl. No. 10/820,635, filed Apr. 8, 2004.
Office Action Response filed on Jan. 11, 2008 U.S. Appl. No. 10/820,635, filed Apr. 8, 2004
Final Office Action issued on Apr. 10, 2008 in U.S. Appl. No. 10/820,635, filed Apr. 8, 2004.
Office Action mailed May 30, 2008 in Chinese Patent Application 200580011803.6 filed Apr. 20, 2005.
Office Action mailed Jul. 25, 2008 in Chinese Patent Application No. 2004-80003472.7 filed Jan. 20, 2004.
Office Action mailed Nov. 5, 2008 in European Patent Application 04703599.3 filed Jan. 20, 2004.
International Search Report and Written Opinion for International Application No. PCT/US2008/080153 dated Jan. 23, 2009.
Request for Continued Examination and Amendment filed on May 11, 2009 in U.S. Appl. No. 10/820,635, filed Apr. 8,2004,
Office Action mailed May 15, 2009 in Japanese Patent Application 2001-511810 filed Jul. 27, 1999.
Office Action mailed May 22, 2009 in Chinese Patent Application 200580011803.6 filed Apr. 20, 2005.
Notice of Allowance issued on May 26, 2009 in U.S. Appl. No. 10/820,635, filed Apr. 8, 2004.
Office Action mailed Jun. 2, 2009, issued in U.S. Appl. No. 11/110,653, filed Apr. 20, 2005.
Office Action mailed Jul. 7, 2009, in U.S. Appl. No. 11/110,968, filed Apr. 20, 2005.
Rejection Decision issued Aug. 14, 2009 in Chinese Patent Application No. 2004-80003472.7 filed Jan. 20, 2004.
Office Action issued on Sep. 10, 2010 in in U.S. Appl. No. 12/499,079, filed Jul. 7, 2009.
Preliminary Amendment filed Oct. 15, 2009 in U.S. Appl. No. 12/499,079, filed Jul. 7, 2009.
Office Action Response filed Dec. 1, 2009 in U.S. Appl. No. 11/110,653, filed Apr. 20, 2005.
Office action mailed Dec. 14, 2009 in European Patent Application 04703599.3 filed Jan. 20, 2004.
Office action mailed Dec. 18, 2009 in Japanese Patent Application 2006-502878 filed Jan. 20, 2004.
Office Action mailed Dec. 25, 2009 in Chinese Patent Application 200580011803.6 filed Apr. 20, 2005.
Office Action Response filed Jan. 7, 2010 in U.S. Appl. No. 11/110,968, filed Apr. 20, 2005.
Office Action mailed Jan. 15, 2010, issued in European Application No. 05737636.0 filed Apr. 20, 2005.
Final Office Action mailed Feb. 1, 2010 in U.S. Appl. No. 11/110,653, filed Apr. 20, 2005.
Office Action mailed Feb. 9, 2010 in Japanese Patent Application 2001-511810 filed Jul. 27, 1999.
International Search Report and Written Opinion for International Application No. PCT/US2009/063651 mailed Mar. 9, 2010.
Office Action issued on Apr. 6, 2010 in corresponding Australian Patent Application No. 2005234778.
International Search Report and Written Opinion issued on Apr. 10, 2010 in connection with corresponding International Application No. PCT/US2008/080153, filed Oct. 16, 2008.
International Search Report and Written Opinion, issued Apr. 30, 2010 in related International Patent Application No. PCT/US08/81584, filed Oct. 29. 2008.
RCE and Amendment filed Jul. 30, 2010 in U.S. Appl. No. 11/110,653, filed Apr. 20, 2005.
Office Action mailed Aug. 20, 2010 in Japanese Application No. 2006-502878.
Restriction Requirement issued Aug. 26, 2010 in U.S. Appl. No. 12/206,974, filed Sep. 9, 2008.
Response to Restriction Requirement filed Sep. 27, 2010 in U.S. Appl. No. 12/206,974, filed Sep. 9, 2008.
Notice of Allowance issued Sep. 28, 2010 in U.S. Appl. No. 11/110,653, filed Apr. 20, 2005.
International Search Report and Written Opinion mailed Oct. 7, 2010 for International Application No. PCT/US2010/041229.
International Search Report and Written Opinion mailed Oct. 7, 2010 for International Application No. PCT/US2010/041242.
Final Office Action mailed Oct. 29, 2010 in U.S. Appl. No. 11/110,968, filed Apr. 20, 2005.
Office Action dated Nov. 2, 2010 in Japanese Application No. 2007-509613 (with English Translation).
Response to Office Action dated Nov. 2, 2010 filed in corresponding Japanese Application No. JP 2007-509613, on Apr. 4, 2011.
Office Action mailed Feb. 28, 2011 in U.S Appl. No. 12/581,061, filed Oct. 16, 2009.
Office Action mailed Feb. 20, 2009 in Chinese Patent Application No. 2004-80003472.7 filed Jan. 20, 2004.
Amendment filed on Mar. 9, 2011 in U.S. Appl. No. 12/499,079, filed Jul. 7, 2009.
Notice of Allowance issued on Mar. 22, 2011 in U.S Appl. No. 12/499,079, filed Jul. 7, 2009.
Office Action mailed in corresponding European Patent Application No. 04703 599.3 on Mar. 23, 2011.
Response to Office Action mailed on Apr. 5, 2011 in corresponding Australian Patent Application No. 2005234778.
Request for Continued Examination, Final Amendment and Summary of Interview, filed in corresponding U.S. Appl. No. 11/110,968 on Apr. 29, 2011.
English Translation of Office Action mailed May 13, 2011 in corresponding Japanese Application No. JP 2006-502878.
Preliminary Amendment filed Jul. 19, 2011 in corresponding U.S. Appl. No. 13/021,594.
Final Office Action issued on Aug. 2, 2011 in corresponding U.S. Appl. No. 12/206,974.
Final Office Action issued on Sep. 6, 2011 in corresponding U.S. Appl. No. 12/581,061.
Response to Office Action filed in corresponding European Patent Application No. 04703 599.3 on Sep. 22, 2011.
Notification of Reasons for Refusal mailed in corresponding Japanese Patent Application No. JP 2007-509613 on Oct. 11, 2011.
Office Action issued in corresponding European Patent Application No. 05737636 on Oct. 27, 2011.
Response to Notification of Reasons for Refusal in corresponding Japanese Patent Application No. JP 2007-509613, filed on Nov. 14, 2011 (with English Translation of Claims).
Request for Continued Examination, Final Amendment and Summary of Interview, filed in corresponding U.S. Appl. No. 12/206,974 on Dec. 2, 2011.
Office Action issued on Jan. 17, 2012 in connection with Canadian Patent Application No. 2,515,010.
Office Action mailed on Jan. 25, 2012 in corresponding U.S. Appl. No. 13/021,594, filed Feb. 4, 2011.
Supplemental Preliminary Amendment filed Feb. 1, 2012 in U.S. Appl. No. 13/363,287, filed Jan. 31, 2012.

(56) References Cited

OTHER PUBLICATIONS

Response to Office Action filed in connection with European European Patent Application No. 05737636 on Feb. 27, 2012.
Request for Continued Examination, Amendment and Terminal Disclaimer filed in connection with U.S. Appl. No. 12/581,061 on Mar. 5, 2012.
Response to Office Action filed in corresponding Japanese Application No. JP 2007-509613, on Mar. 8, 2012.
Decision to Grant issued on Mar. 13, 2012 in connection with Japanese Patent Application No. 2007-509613.
Notice of Allowance issued on Mar. 20, 2011 in connection with U.S. Appl. No. 12/581,061 on Mar. 5, 2012.
Request for Continued Examination and IDS filed in connection with U.S. Appl. No. 12/206,974 on Mar. 21, 2012.
Notice of Allowance issued in corresponding U.S. Appl. No. 12/206,974 on Dec. 22, 2011.
Extended Search Report issued on Mar. 26, 2012 in connection with European Patent Application No. 12151139.8
Office Action issued on Mar. 26, 2012 in connection with European Application No. EP 05737636.
Decision of Rejection (and English Translation) issued on May 11, 2012 in corresponding Japanese Patent Application No. JP 2006-502878.
Office Action issued on May 16, 2012 in connection with U.S. Appl. No. 12/614,344, filed Nov. 6, 2009.
Response to Office Action filed on May 22, 2012 in corresponding U.S. Appl. No. 13/021,594.
Restriction Requirement issued on Jun. 8, 2012 in corresponding U.S. Appl. No. 12/835,665.
Response to Restriction Requirement filed on Jul. 6, 2012 in corresponding U.S. Appl. No. 12/835,665.
Notice of Allowance issued on Jul. 11, 2012 in corresponding U.S. Appl. No. 13/021,594.
Office Action Response filed Jul. 17, 2012 in connection with corresponding Canadian Patent Application No. CA 2515010.
Notice of Allowance issued on Jul. 18, 2012 in corresponding U.S. Appl. No. 12/581,061.
Notice of Allowance issued on Aug. 6, 2012 in connection with corresponding U.S. Appl. No. 12/206,974, filed Sep. 9, 2008.
Non-Final Office Action issued on Aug. 24, 2012 in corresponding U.S. Appl. No. 12/835,668.
Preliminary Amendment filed on Sep. 14, 2012 in corresponding U.S. Appl. No. 13/750,080.
Notice of Allowance issued on Sep. 17, 2012 in corresponding Canadian Application No. CA 2,515,010.
Response to Office Action dated Mar. 26, 2012, mailed on Oct. 4, 2012 in corresponding Application No. EP 05737636.
Non-Final Office Action issued on Oct. 5, 2012 in U.S. Appl. No. 12/835,665.
Request for Continued Examination filed on Oct. 10, 2012 in corresponding U.S. Appl. No. 13/021,594.
Office Action issued on Oct. 25, 2012 in connection with corresponding U.S. Appl. No. 12/581,074.
Office Action issued on Oct. 26, 2012 in connection with corresponding U.S. Appl. No. 13/619,168.
Notice of Allowance issued on Oct. 30, 2012 in connection with corresponding U.S. Appl. No. 13/021,594.
Office Action issued on Nov. 5, 2012 in connection with corresponding U.S. Appl. No. 12/830,221.
Preliminary Amendment filed on Dec. 3, 2012 in corresponding U.S. Appl. No. 13/620,593.
Office Action issued on Dec. 17, 2012 in corresponding U.S. Appl. No. 12/614,344.
European Search Report issued Dec. 21, 2012 in corresponding European Application No. 10800338.
Extended Search Report issued on Jan. 8, 2013 in connection with European Patent Application No. 10800335.
Office Action issued on Feb. 12, 2013 in connection with related Canadian Patent Application No. 2,561,388.
Final Office Action, issued on Feb. 19, 2013, in corresponding U.S. Appl. No. 12/835,668.
Office Action issued on Feb. 25, 2013, in corresponding U.S. Appl. No. 12/740,753.
Terminal Disclaimer and Interview Summary submitted on Feb. 27, 2013 in corresponding U.S. Appl. No. 13/619,168.
Office Action Response filed on Mar. 5, 2013 in corresponding U.S. Appl. No. 12/830,221.
"IOL Power Calculations Piggyback Lens," http://doctor-hill.com/iol-main/piggyback.html, accessed on Feb. 24, 2010.
"Refractive Vergence Formula Piggyback IOL Intraocular Lens Calculations," http://doctor-hill.com/iol-mail/piggyback.html, accessed on Feb. 12, 2010.
Aramberri, "Intraocular lens power calculation after corneal infrastructure surgery: Double-K method," J Cataract Refract Surg 29:2063-2068 (Nov. 2003).
Argento et al., "Intraocular lens power calculation after refractive surgery," J Cataract Refract Surg 29:1346-1351 (Jul. 2003).
Binkhorst RD., "Intraocular lens power calculation", Int Ophthalmol Clin. 1979 Winter; 19(4):237-52. (Abstract).
Binkhorst, "Power of the Pre-Pupillary Pseudoshakos," B.J.O. 56:332-37 (1972).
Binkhorst, "The Optical Design of the Intraocular Lens Implants," Opthalmic Surg 6(3): 17-31 (1975).
Brandser R., "Accuracy of IOL calculation in cataract surgery", Acta Ophthalmol Scand. Apr. 1997; 75(2):162-5 (Abstract).
Chen et al., "Analysis of intraocular lens power calculation in post-radial keratotomy eyes," J Cataract Refract Surg 29:65-? (Jan. 2003).
Colenbrander, "Calculation of the Power of an Iris-Clip Lens for Distance Vision," Br. J. Ophthal. 57:735-40(1973).
Cordonnier, M., et al., "How accurate is the hand-held refractor Retinomax(R) in measuring cycloplegic refraction: a further evaluation", Strabismus Sep. 1998;6(3):1337-I42 (Abstract).
Cua et al., Intraocular lens calculations in patients with corneal scarring and irregular astigmatism, J Cataract Refract Surg 29:1352-1357 (Jul. 2003).
Dalens H, Marcellier JJ, Moussiere L., "Use of the SRK (Sanders-Retzlaff-Kraft) regression formula in the preoperative calculation of the power of crystalline implants" (Abstract).
Donoso R., et al., "Emmetropization at cataract surgery. Looking for the best IOL power calculation formula according to the eye length", Arch Soc Esp Oftalmol. Sep. 2003;78(9):477-80 (Abstract).
El-Baha SM, et al., "Intraoperative biometry for intraocular lens (IOL) power calculation at silicone oil removal", Eur J Ophthalmol. Aug.-Sep. 2003;13(7):622-6. (Abstract).
El-Defrawy S., et al. "Evaluation of a hand-held autorefractor in children younger than 6", J Pediatr Ophthalmol Strabismus, Apr. 1998~ar-;35(2):107-9 (Abstract)
Feiz, et al., "Intraocular Lens Power Calculation After Laser In Situ Keratomileusis for Myopia and Hyperopia—A Standard Approach," Cornea 20(8):792-797 (2001).
Feordorov et al. "Estimation of Optical Power of the Intraocular Lens," Vestn. Onamol 80(4):27-31 (1967).
Filip M., et al. "Post-operatory biometry and refraction results estimated and refraction surprises—clinical study", Oftalmologia.2003. 56(1):11-4 (Abstract).
Gernet, "IOL Calculation According to Gernet and the GOW 70 PC Programme," Abstract from Ophthalmologe 98:873-876 (2001).
Gimbel et al., "Accuracy and Predictability of Intraocular Lens Power Calculation After Laser In Situ Keratomileusis," J Cataract Refract Surg 27:571-576 (Apr. 2001).
Gimbel et al., "Accuracy and Predictability of Intraocular Lens Power Calculation After photorefractive keratectomy," J Cataract Refract Surg 26:1147-1151 (Apr. 2000).
Gupta, et al., "Design and use of an infrared Pupilometer for real-time pupil mapping in response to incremental illumination levels," 2000 Optical Society of America; Total 4 pages.
Guttman, "Aberrometer Aims to Improve Refractive, Cataract Outcomes—Investigational Device Allows Evaluation of Wide Range of Eyes", Opthamology Times, Oct. 15, 2008, accessed Feb. 23, 2010, URL http://www.modernmedicine.com/modernmedicine/Refractive+Surgery+Feature/Aberrometer-aims-to-improve-refractive-cataract-ou/Article Standard/Article/detail/559856.

(56) References Cited

OTHER PUBLICATIONS

Hamilton et al., "Cataract Surgery in Patients with Prior Refractive Surgery", Current Opinion in Ophthalmology 14:44-53 (2003).
Happe W. et al., "Intraoperative Skiaskopie zur Bestimmung des Brechwerts einer zu implantierenden Intraokularlinse" [Intraoperative retinoscopy for determining the refractive value of an implantable intraocular lens] Klin. Monatsbl. Augenheilkd. vol. 210, No. 4. 1997, pp. 207-212.
Harvey et al., "Reproducability and accuracy of measurements with a hand held autorefractive in children," Journal of Opthalmology 81:941-948 (1997).
Hoffer KJ, et al., "A simple lens power calculation program for the HP-67 and HP-97 Calculators", JAm Intraocul Implant Soc. Oct. 1978; 4(4):197-9. (Abstract).
Hoffer, "Calculating Corneal Power After Refractive Surgery," Cataract & Refractive Surgery Today 4(4):23-25 (Apr. 2004).
Hoffer, "Mathematics and computers in intraocular lens calculation," Am Intra-Ocular Implant Soc. J. 1(1):4-5 (1975).
Holladay, et al., "A three-part system for refining intraocular lens power calculations," J. Cataract Refract Surg. 14:17-24 (Jan. 1988).
Holladay, Jack T., "Refractive Power Calculations for Intraocular Lenses in Phakic Eye," American Journal of Ophthalmology, Jul. 1993, pp. 63-66.
Holladay, JT et al., Refining Toric Soft Contact Lens Prescriptions. CLAO J, 1984, 10:326-31.
Holladay, JT, et al. "Calculating the Surgically Induced Refractive Change Following Ocular Surgery", J. Cataract Refract. Surg. 1992; 18:429-43.
http://www.wavetecvision.com/ accessed Feb. 24, 2010.
Hunt et al., "Evaluation of the measurement of refractive error by the PowerRefractor: a remote, continuous and binocular measurement system of oculomotor function," Br. J. Opthalmol 87:1504-1508 (2003).
Ianchulev, "Method for Intraoperative Refractive IOL Calculation," Poster Presentation at Ophthalmology Conference (Apr. 2004).
Ianchulev, et al. (Aug. 2005), "Intraoperative optical refractive biometry for intraocular lens power estimation without axial length and keratometry measurements," Journal of Cataract & Refractive Surgery, vol. 31, Issue 8, pp. 1530-1536, Abstract.
Isenberg et al., "Use of the HARK Autorefractor in Children," American Journal of Ophthalmology 131(4):438-441 (2001).
Iuorno JD, et al., "Clinical comparison of the Welch Allyn SureSight handheld auto refractor versus cycloplegic auto refraction and retinoscopic refraction", J AAPOS. Apr. 2004;8(2):123-7 (Abstract).
Ivanov MN, et al., "Formula for calculating the IOL focal power", Vestn Oftalmol. Jul.-Aug. 2003;119 (4):52-4 (Abstract).
Iwami S. et al., "Prediction of Postoperative Refraction Using Intraoperative Retinoscopy" Journal of Japanese Ophthalmological Society, vol. 103, No. 7, 1999, pp. 551-555.
Koo, So, et al., "Comparison of IOL powers by corrected method in eyes after PRK and LASIK", Korean J Ophthalmol. Jun. 2002;16(1):26-31 (Abstract).
Kora et al., "Intraocular lens power calculation for lens exchange," J Cataract Surg 27:543-548 (Apr. 2001).
Liang, et al. "Comparison of the handheld Retinomax K-Plus 2 and on-table autokeratometers in children with and without cycloplegia," J Cataract Refract Surg 30:670-674 (Mar. 2004).
Liang, et al. "Aberrations and Retinal Image Quality of the Normal Human Eye", J. Optical Society of America, vol. 14, No. 11, Nov. 1997.
Liang, et al. "Comparison of Measurements of Refractive Errors Between the Hand-held Retinomax and On-table Autorefractors in Cyclopleged and Noncyclopleged Children," American Journal of Ophthalmology 136(6): 1120-1128 (Dec. 2003).
Lipatov DV., "Assessment of the efficiency of different formulae applied to calculating the optic power of an intraocular lens in transscleral fixation", Vestn Oftalmol, Nov.-Dec. 2003; 119(6)3-5 (Abstract).
Ma, et al., "Simple method for accurate alignment in toric phakic and aphakic intraocular lens implantation," J Cataract Refract Surg, Technique, Oct. 2008, vol. 34, pp. 1631-1636.
Mackool RJ., "The cataract extraction-refraction-implantation technique for IOL power calculation in difficult cases", J Cataract Refract Surg. Apr. 1998;24(4):434-5 (Abstract).
Masket, et al., "Atlas of Cataract Surgery," Book cover in 1 page, Front Matter in 11 pages. (Table of Contents in 3 pages), Chapter 19 pp. 147-158, Published by Martin Dunitz Ltd 1999, United Kingdom.
Methling D, Kalb G., "A New Program for Calculating Intraocular Lenses", Klin Monatsbl Augenheilkd. Oct. 1992;201 (4):247-53 (Abstract).
Moreno-Barriuso, et al., "Laser Ray Tracing Versus Hartmann-Shack Sensor for Measuring Optical Aberrations in the Human Eye", J. Optical Society of America, vol. 17, No. 6, Jun. 2000.
Nemeth et al., "Optical and ultrasound measurement of axial length and anterior chamber depth for intraocular lens power calculation," J Cataract Refract Surg 29;85-88 (Jan. 2003)
Olsen, "Theoretical approach to intraocular lens calculation using Gaussian optics," J Cataract Refract Surg 13:141-145 (Mar. 1987).
Olsen, "Theoretical computer-assisted prediction versus SRK prediction of postoperative refraction after intraocular lens implantation," J Cataract Refract Surg 13:141-145 (Mar. 1987).
Orr et al., "Manifest Refraction Versus Autorefraction for Patients with Subfoveal Choroidal Neovascularization," Investigative Ophthalmology & Visual Science 42(2): 447-451 (Feb. 2001)
Oyo-Szerenyi et al., "Autorefraction/Autokeratometry and Subjective Refraction in Untreated and Photorefractive Keratectomy—Treated Eyes," Arch Ophthalmol, vol. 115 (Feb. 1997).
Photograph of Oculus Instrument, accessed at http://www.oculus.de/en/sites/popup_bild_gross.php?news=&id=1056 on Apr. 29, 2011.
Quiroga, et al., "*Fourier transform method for automatic processing of moire deflectograms*,"Jun. 1999, Society of Photo-Optical Instrumentation Engineers, pp. 974-982.
Raj et al., "Clinical evaluation of automated refractio in anterior chamber pseudophakia," British Journal of Ophthalmology 75:42-44 (1991).
Raj et al., "Objective autorefraction in posterior chamber pseudophakia," British Journal of Ophthalmology 74:731-733 (1990).
Raj PS, et al., "Comparative evaluation of the Allergan Humphrey 570 and Canon RK-I autorefractors: I. Objective autorefraction in normal subjects", Eye 1992;6 (Pt 3):284-6 (Abstract).
Retzlaff J., "A new intraocular lens calculation formula", J Am Intraocul Implant Soc. Apr. 1980 6(2):148-52. (Abstract).
Rubin A., et al., "Refractive variation during autorefraction: multivariate distribution of refractive status", Optom Vis Sci. Jun. 1995;72(6):403-10 (Abstract).
Rubin A., et al., "Variation during autorefraction: influence of two different target types", Ophthalmic Physiol Opt. Jan. 1997;17(1):38-43 (Abstract).
Sanders et al., "Comparison of the SRK/T formula and other theoretical and regression formulas," J Cataract Refract Surg. 16:341-346 (May 1990).
Sanders et al., "Comparisons of the SRK™ formula and other second generation formulas," J Cataract Refract Surg 14:136-141 (Mar. 1988).
Senjo, et al., "Prediction of Postoperative Refraction Using Intraoperative Retinoscopy," Journal of Japanese Ophthalmological Society, 1999, vol. 103, No. 7, pp. 551-555, Abstract.
Siahmed K., et al., "Optic biometry in intraocular lense calculation for cataract surgery. Comparison with usual methods", J Fr Ophtalmol. Nov. 2001;24(9):922-6 (Abstract).
Siganos et al., "Autorefractometry after laser in situ keratomileusis," J Cataract Refract Surg 29:133-137 (Jan. 2003).
Steele, G., et al., "Cycloplegic auto refraction results in pre-school children using the Nikon Retinomax Plus and the Welch Allyn SureSight", Optom Vis Sci. Aug. 2003;80(8):573-7 (Abstract).
Straub et al., "*Design of a compact Shack-Hartmann aberrometr for real-time measurement of aberrations in human eyes*," 2000 Optical Society of America, pp. 110-113.
Supplemental Amendment filed Apr. 1, 2010 in U.S. Appl. No. 11/110,968, filed Apr. 20, 2005.

(56) References Cited

OTHER PUBLICATIONS

Supplementary European Search Report for Application No. 05737636.0, Dated Mar. 19, 2009.
Suto et al., "Adjusting intraocular lens power for sulcus fixation," J Cataract Refract Surg 29:1913-1917 (Oct. 2003).
Thall et al., "Linear Regression Software for Intraocular Lens Implant Power Calculation," American Journal of Ophthalmology 101:597-599 (May 1986).
Thijssen JM., "The emmetropic and the iseikonic implant lens: computer calculation of the refractive power and its accuracy", Ophthalmologica. 1975;171 (6):467-86 (Abstract).
Thompson et al., "A New Posterior Chamber Intraocular Lens Formula for Axial Myopes," Ophthalmology 91(5): 484-488 (May 1984).
Tromans et al., "Accuracy of intraocular lens power calculation in paediatric cataract surgery," Br J Ophthalmol 85:939-941 (2001).
Tseng, et al., "Calculating the optimal rotation of a misaligned toric intraocular lens," J Catactact Refract Surg, Laboratory Science, Oct. 2008, vol. 34, pp. 1767-1772.
Villada Jr., et al., "Comparative evaluation of the Allergan Humphrey 570 and Canon RK-I autorefractors: II, Objective autorefraction in pseudophakes", Eye. 1992;6 (Pt 3):287-9 (Abstract).
Walline JJ, "Repeatability and validity of astigmatism measurements", J Refract Surg. Jan.-Feb. 1999; 15(1):23-31 (Abstract).
Wiechens, et al., "Bilateral Cataract after Phakic Posterior Chamber Top Hat-style Silicone Intraocular Lens," Journal of Refractive Surgery, Jul./Aug. 1997, vol. 13, No. 4, Cover and Table of Contents in 2 pages, pp. 392-397.
Wood IC., "A review of autorefractors", Eye. 1987;1 (Pt 4):529-35 (Abstract).
Yalvac IS, et al., "Calculation of intraocular lens power with the SRK IIformula for axial high myopia" Eur J Ophthalmol. Oct.-Dec. 1996;6(4):375-8 (Abstract).
Zaldivar et al., "Intraocular lens power calculations in patients with extreme myopia" Cataract Refract Surg 26:668-674 (May 2000)
Rosales et al., "Phakometry and lens tilt and decentration using a custom-developed Purkinje imaging apparatus. validation and measurements," Journal of the Optical Society of America, vol. 23, No. 3, Mar. 2006, pp. 509-520.
Castro et al., "Tilt and decentration of intraocular lenses in vivo from Purkinje and Scheimpflug imaging: Validation study," J. Cataract Refract. Surg. 2007; 33:418-429.
Tabernero et al., "Instrument for measuring the misalignments of ocular surfaces," Optical Society of America, Oct. 30, 2006, vol. 14, No. 22.
Uozato et al., "Intraoperative Confirmation Device for IOL Centering," Folia Ophthalmological Japonica, vol. 41, 1990, pp. 1325-1329.
Responses to Office Action filed in corresponding U.S. Appl. No. 12/581,061, on Jun. 28, 2011.
Response to Office Action filed Jan. 25, 2013 in connection with related U.S. Appl. No. 12/581,074.
Response to Office Action filed Jan. 28, 2013 in connection with related U.S. Appl. No. 13/619,168.
Office Action issued on Apr. 4, 2013, in corresponding EP Application No. 12 151 139.8.
Office Action issued May 9, 2013 in connection with U.S. Appl. No. 12/581,074.
Notice of Allowance issued on May 16, 2013 in corresponding U.S. Appl. No. 13/619,787.
Request for Continued Examination and Response to Office Action filed Aug. 9, 2013 in corresponding U.S. Appl. No. 12/581,074.
European Examination Report re EP Application No. 10 800 338.5, dated Dec. 18, 2013.
Chinese Office Action and Search Report re CN Application No. 201080040737.6, dated Dec. 20, 2013.
Japanese Office Action issued on Feb. 4, 2014 re JP Application No. 2012-520669.
Notice of Allowance issued on Feb. 20, 2014 in corresponding U.S. Appl. No. 12/835,668.
Canadian Office Action, re CA Application No. 2,561,388, dated May 12, 2014.
Chinese Notice of Allowance re CN Application No. 201080040737.6, dated Aug. 28, 2014.
Office Action issued on Oct. 17, 2014, in corresponding U.S. Appl. No. 13/797,365.
European Extended Search Report, re EP Application No. 14181278.4, dated Dec. 3, 2014.
Japanese Office Action issued on Jan. 6, 2015, with Translation, re JP Application No. 2012-520669.
Notice of Allowance issued on Apr. 15, 2015, in corresponding U.S. Appl. No. 13/797,365.
CA Office Action re Application No. CA 2,561,388, dated May 27, 2015.
Notice of Allowance issued on Jun. 23, 2015, in corresponding U.S. Appl. No. 12/581,074.
Nanavaty, et al.: "Anterior capsule cover and axial movement of intraocular lens," Eye (2008) 22, 1015-1023.
Narvaez et al.: "Accuracy of intraocular lens power predictin using the Hoffer Q, Holladay 1, Holladay 2, and SRK/T formulas," Journal of Cataract & Refractive Surgery, Dec. 2006.
Sandstedt, et al.: "Corneal endothelial safety after ultraviolet light treatment of the light-adjustable intraocular lens," J. Cataract Refract. Surg. 2011; 37:324-327.
Van Heugten, T., et al. "Validation of Novel Hartmann-Moire Wavefront Sensor with Large Dynamic Range", presented at Wavefront Congress, Feb. 17, 2008, available at http://www.wavefront-congress.org/info/listing_detail.asp?absID-12, last visited Feb. 28, 2008.

* cited by examiner

OPHTHALMIC SURGERY MEASUREMENT SYSTEM

CROSS-REFERENCE TO RELATED APPLICATIONS

This application is a continuation of U.S. patent application Ser. No. 12/835,665, filed Jul. 13, 2010, and entitled "OPHTHALMIC SURGERY MEASUREMENT SYSTEM," which claims priority to U.S. Provisional Patent Application 61/225,547, filed Jul. 14, 2009, and entitled "OPHTHALMIC SURGERY MEASUREMENT SYSTEM," both of which are hereby incorporated by reference herein in their entirety.

BACKGROUND OF THE INVENTION

1. Field of the Invention

Embodiments of the invention relate generally to systems and methods for performing ophthalmic measurements. In particular, some embodiments can be used for measuring a spatial distance in a patient's eye such as, for example, the distance between the corneal surface and the posterior wall of the capsular bag in an aphakic eye.

2. Description of the Related Art

Various ophthalmic procedures involve measurements of a spatial distance within a patient's eye, including measurements of the dimensions of the eye, or dimensions of features of the eye, the distance between selected portions or features of the eye, etc. For example, such measurements can be of the anterior chamber depth (ACD), lens thickness, and axial length of the eye. Techniques for making certain types of these measurements include ultrasonic measuring and Optical Coherence Tomography (OCT). Despite the successes of these techniques in various ophthalmic applications, there is a continuing need for improved techniques and systems for measuring spatial distances within the eye.

SUMMARY OF THE INVENTION

Various embodiments disclosed herein include an ophthalmic apparatus. The ophthalmic apparatus can include a first laser configured to direct a first beam of light into an eye of a patient at a first non-zero angle with respect to an optical axis of the apparatus, such that the first beam of light propagates to a target area within the eye, and such that a portion of the first beam of light is scattered by the target area. The apparatus can also include imaging optics positioned to receive light scattered by the target area, and the imaging optics can define the optical axis of the apparatus. The apparatus can also include a photosensitive element, wherein the imaging optics direct the light scattered from the target area to the photosensitive element. The apparatus can also include a processor configured to determine a distance between the cornea of the eye and the target area within the eye based at least in part on the light received by the photosensitive element.

Various embodiments disclosed herein include a method of determining the optical power for an intraocular lens to be implanted into an eye. The method can include measuring an intraoperative characteristic of the eye. The intraoperative characteristic can include the distance between selected first and second portions of the eye. The method can also include determining the optical power for the intraocular lens based at least in part on the measured intraoperative characteristic.

Various embodiments disclosed herein include a method of using an ophthalmic apparatus. The method can include positioning the ophthalmic apparatus at a predetermined position over an eye of a patient, wherein an optical axis of the apparatus intersects the cornea of the eye. The method can include directing light from one or more lasers positioned about the optical axis of the apparatus into the eye so that a portion of the light from the one or more lasers is scattered by a target area inside the eye. The method can include directing a portion of the light scattered by the target area to a photosensitive element using imaging optics that define the optical axis. The method can include forming one or more target spots on the photosensitive element, and the one or more target spots can correspond to the light from the respective one or more lasers scattered by the target area. The method can also include calculating the distance between the cornea of the eye and the target area based at least in part on the positions of the one or more target spots.

DETAILED DESCRIPTION OF THE PREFERRED EMBODIMENT

Figure 1:
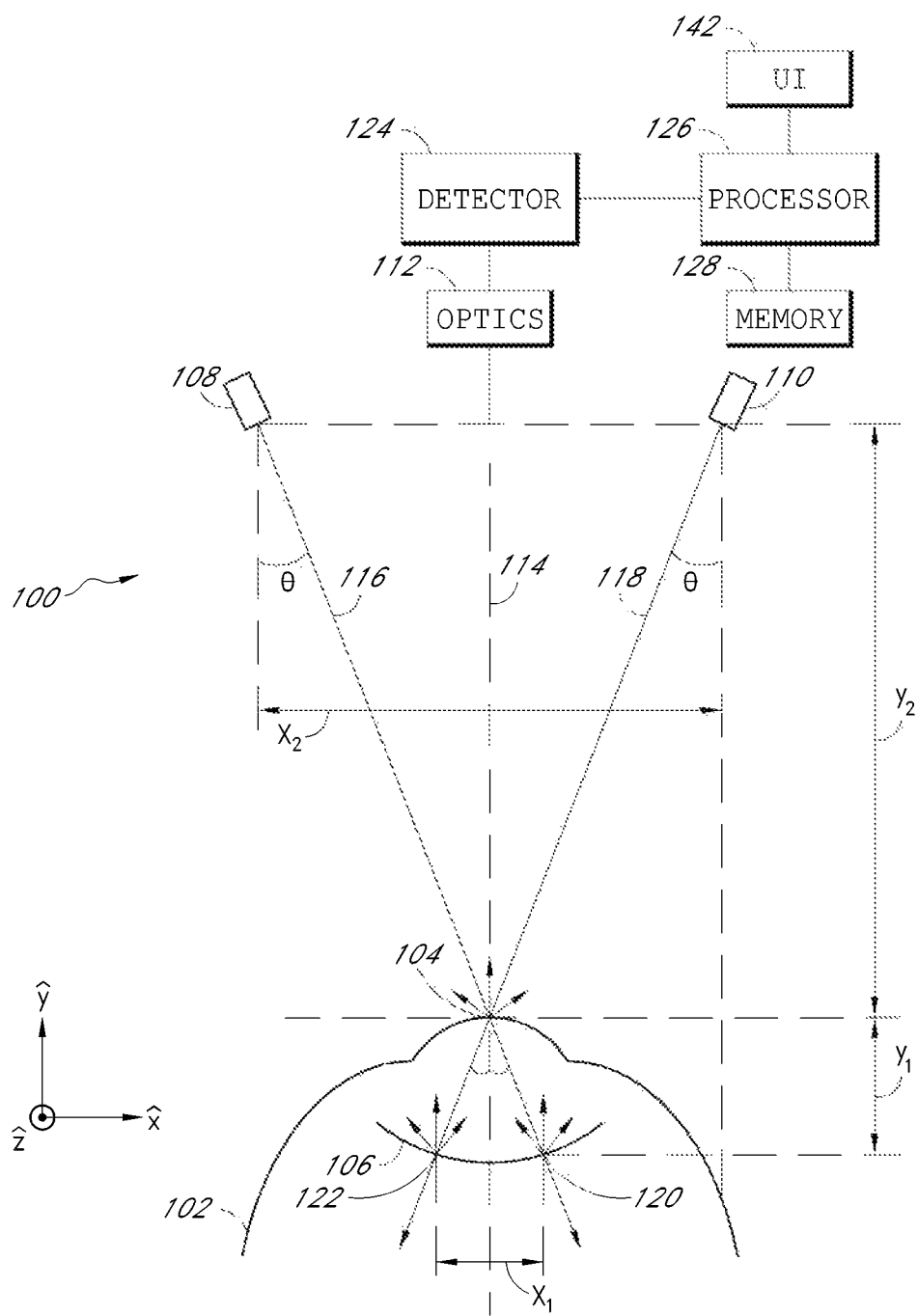
FIG. 1 schematically illustrates an embodiment of an ophthalmic measurement system for measuring dimensions of or in a patient's eye including, for example, the distance between the cornea and a posterior wall of the capsular bag in an aphakic eye.

In a typical intraocular lens (IOL) implantation surgery, a surgeon removes the natural crystalline lens from a patient's eye and an IOL is implanted in its place. IOL implantation surgery can be performed, for example, on a patient suffering from cataracts. By selecting an IOL having an appropriate power, an eye that prior to the surgery was, for example, myopic (near sighted), hyperopic (far sighted), and/or astigmatic can be restored to an emmetropic condition. Various factors can be considered when calculating the appropriate power for the IOL, such as 1) the axial length of the eye, measured from the corneal surface to the retina; 2) the total optical power of the cornea; 3) the desired postoperative optical power (e.g., 0.0 diopters (D) for an emmetropic eye); and the effective lens position (ELP) of the IOL, which can be understood, for example, as the distance from the corneal surface to the post-operative position of the IOL. The axial length of the eye can be measured preoperatively (e.g., before the patient has been located on the operating table in a supine position), for example, by an ultrasound device or by Optical Coherence Tomography (OCT). The optical power of the cornea can be estimated from the corneal curvature values (Ks) of the eye measured preoperatively by a keratometer. Alternatively, or in addition, the total refractive power of the aphakic eye, which is a function of corneal curvature and axial length of the eye, can be measured intraoperatively and used in the IOL power calculation.

The ELP of the IOL has traditionally been difficult to determine. The ELP of the IOL can be estimated based on preoperative data, but such estimates are limited in their accuracy. The limited accuracy of ELP estimates based on preoperative data can be attributed, at least in part, to the implanted IOL being positioned in the capsular bag differently than the natural crystalline lens. Preoperative measurements of the crystalline lens position do not always correlate well with the actual postoperative position of the IOL. Cataractous crystalline lenses vary in shape and size from individual to individual. In some patients, preoperative measurements (e.g., the ACD, which can be understood as, for example, the distance from the corneal surface to the anterior lens surface plus half the lens thickness) may provide a reasonable estimate of the ELP, but in other patients this is not the case due to the differing shapes of cataractous lenses in patients.

Some efforts have been made to develop formulas to estimate the ELP of the IOL based on preoperative information, such as direct measurements of the axial length and corneal curvature of the patient's eye. Such formulas include the Holladay 1, SRK/T, Hoffer Q, Holladay 2, and Hagis formulas. Generally speaking, these formulas are based on statistical regression analysis of the relationship between pre-operative characteristics of the eye and the surgical outcome. These formulas sometimes produce estimates of the ELP of the IOL with insufficient accuracy, especially in those patients with axial lengths outside the normal range, resulting in suboptimal surgical results, for example, wherein the patient's eye is not restored to an emmetropic condition. These formulas all attempt to determine how an individual patient may vary from the average of a large population to estimate the ELP. The factors used by these formulas to estimate the ELP for a particular patient are not factors that directly relate to the lens position.

Given the sometimes-insufficient level of correlation between estimates of the ELP for an IOL and characteristics of the eye that can be measured preoperatively (e.g., corneal curvature, axial length, etc.), it would be desirable to estimate the ELP for the IOL based on characteristics of the eye that are more closely correlated with ELP, such as certain intraoperative characteristics of the eye. One such intraoperative characteristic of the eye is the location of the aphakic capsular bag within the eye (e.g., the longitudinal distance from the anterior corneal apex to the posterior wall of the aphakic capsular bag). The location of the aphakic capsular bag is an example of an intraoperative characteristic of the eye that is believed to be more closely correlated with the ELP of the IOL than are the preoperative characteristics of the eye from which the Holladay 1, SRK/T, Hoffer Q, Holladay 2, and Hagis formulas estimate the ELP of the IOL. This is at least in part due to the fact that an aphakic measurement of the distance from the cornea to the posterior wall of the capsular bag is not tainted by the irregular size and shape of the caratactous lens. Regression analysis can be used to establish the correlation between the location of the aphakic capsular bag and the postoperative position of the IOL. Because the location of the aphakic capsular bag is believed to be closely correlated with the ELP, measuring the location of the aphakic capsular bag can reduce the complexity of ELP calculations. For example, in some embodiments, the ELP can be calculated by subtracting a constant from the measured distance from the cornea to the posterior wall of the aphakic capsular bag, wherein the constant is determined by the regression analysis of postoperative IOL lens position or other outcome analysis. Various other formulas can be used to calculate the ELP.

In some embodiments, an ophthalmic apparatus is provided to perform intraoperative measurements of spatial distances of/within a patient's eye. For example, these intraoperative measurements can be measurements of the patient's aphakic eye. These intraoperative measurements can be used to calculate an improved estimate of the ELP of the IOL, the improved estimate being a result of closer correlation between the intraoperative measurement and the ELP of the IOL than the correlation between preoperative measurements and the ELP of the IOL. For example, in some embodiments, the ophthalmic apparatus measures a distance between the cornea and the aphakic capsular bag. This distance can be between a selected position or portion of the cornea and a selected position or portion of the aphakic capsular bag. The selected portion of the cornea can be, for example, the location on the corneal surface where the visual axis of the eye intersects the corneal surface and/or the location where the corneal surface is perpendicular to the visual axis. The selected portion of the cornea can be other locations as well, such as the corneal apex. The selected portion of the capsular bag can be, for example, all or a portion of its posterior wall, all or a portion of its anterior wall, etc.

In some embodiments, the ophthalmic apparatus measures the aphakic capsular bag depth which can be understood, for example, as the distance from the cornea of the eye to the posterior or anterior surface of the capsular bag in an aphakic eye. An aphakic eye is an eye in which the lens of the eye is absent, while a phakic eye has the natural crystalline lens contained therein. The ophthalmic apparatus can be used during an IOL implantation surgery after the natural crystalline lens has been removed from the eye. The measured aphakic capsular bag depth can be used to predict the postoperative position of the IOL with greater accuracy than traditional methods, allowing the surgeon to more accurately calculate the appropriate power for the IOL to be implanted during the surgical procedure. In some embodiments, the actual IOL postoperative position can be measured after the IOL has been implanted (e.g., using OCT or an ultrasound device), and that data can be used to improve the correlation between aphakic capsular bag depth and postoperative IOL position.

FIG. 1 schematically illustrates an embodiment of an ophthalmic measurement system 100 for measuring dimensions of or in a patient's eye 102. In FIG. 1, the ophthalmic measurement system 100 is shown configured to measure the distance $y_1$ between the corneal surface 104 of the eye 102 and the posterior wall of the capsular bag 106. In some embodiments, the eye is aphakic, the natural crystalline lens having been removed from the eye beforehand, such as during an IOL implantation surgery procedure. This measurement can be performed, for example, intraoperatively before or after the globe and capsular bag have been inflated (e.g., with basic saline solution or visco-elastic material).

For convenience, a three-dimensional coordinate system can be defined having a y-axis parallel to the visual axis of the patient's eye 102, and x- and z-axes that are mutually orthogonal to the y-axis so that the x- and z-axes define a plane that is perpendicular to the visual axis of the eye. In the context of this three-dimensional coordinate system, lateral positioning of the ophthalmic measurement system 100 corresponds to the x and z coordinates of the ophthalmic measurement system 100, while longitudinal positioning corresponds to the y coordinate of the ophthalmic measurement system 100. It should be understood that the coordinate system described is for illustrative purposes only and other coordinate systems and other configurations can be used. For example, in some embodiments, the y-axis can be parallel with the optical axis of the patient's eye 102 and the x- and z-axes can define a plane that is perpendicular to the optical axis of the patient's eye 102.

The ophthalmic measurement system 100 can include optics system 112 for collecting, directing, and/or focusing light that is scattered by the eye 102 during a measurement process. The optics system 112 can define an optical axis 114 of the ophthalmic measurement system 100. In some embodiments, the ophthalmic measurement system 100 can be positioned at a predetermined position relative to the patient's eye 102. For example, the ophthalmic measurement system 100 can be positioned laterally so it is centered over the pupil of the eye, and/or so that the optical axis 114 is substantially collinear with the visual or optical axis of the eye 102. The ophthalmic measurement system 100 can be positioned longitudinally so that it is located at a predetermined distance from the eye 102. As discussed in greater detail below, the ophthalmic measurement system 100 can be used in conjunction with a positioning system (not shown in FIG. 1) for accurately positioning the ophthalmic measurement system 100 at the desired position.

The ophthalmic measurement system 100 can include a pair of lasers 108, 110 oriented to direct light into the patient's eye. In some embodiments, the lasers 108, 110 produce light that is outside of the visible spectrum (e.g., infrared light). For example, 780 nm free space lasers can be used, such as those available from Blue Sky Research of Milpitas, Calif. In some embodiments, the lasers 108, 110 produce beams of light having a width of at least about 200 microns and/or less than about 1000 microns, although widths outside this range may also be used. The lasers 108, 110 can be positioned on opposite sides of the optical axis 114, and can be separated by a distance $x_2$. In some configurations the lasers 108, 110 are positioned so that the optical axis 114 is located substantially at a midpoint between the lasers 108, 110, though this is not required. In some embodiments, the lasers 108, 110 are separated by a distance of at least about 60 mm and/or less than about 80 mm, although distances outside this range can also be used.

In some embodiments, when positioned at the desired location with respect to the eye 102, the lasers 108, 110 are located at a distance $y_2$ from the corneal surface of the eye. In some embodiments, the lasers 108, 110 can be positioned at a distance of at least about 100 mm and/or less than about 150 mm from the corneal surface 104, although distances outside this range can also be used. In an example embodiment, the lasers 108, 110 are positioned about 128 mm from the corneal surface 104 of the eye 102. In some embodiments, the lasers 108, 110 are positioned substantially equidistant from the eye 102. In other embodiments, one laser (e.g., 108) is positioned closer to the eye 102 than the other laser (e.g., 110).

In some embodiments, the lasers 108, 110 are oriented so that their respective emitted beams 116, 118 are coplanar. The lasers 108, 110 can be oriented (e.g., based on a predetermined distance $y_2$) so that the beam of light 116 emitted by the laser 108 is directed along a path that intersects the corneal surface 104 of the eye 102 at the location where the visual axis of the eye intersects the corneal surface 104, and so that the beam of light 118 emitted by the laser 110 is directed along a path that intersects the cornea of the eye at the corneal location where the visual axis of the eye intersects the corneal surface 104. Thus, the beams of light 116, 118 emitted by the lasers 108, 110 can intersect at the center of the corneal surface 104 of the eye 102. The lasers 108, 110 can be oriented so as to emit the beams of light 116, 118 at a non-zero angle θ with respect to the optical axis 114. In some embodiments, the beams of light 116, 118 deviate from the optical axis 114 by an angle of at least about 13° and/or less than about 17°, although angles outside this range may also be used. In some embodiments, the beams of light 116, 118 emitted by the lasers 108, 110 deviate from the optical axis 114 by substantially the same amount, but in substantially opposite directions, though the angle between each beam and the optical axis 114 need not be identical. In some embodiments, the angles by which the beams of light 116, 118 deviate from the optical axis are within 10°, 5°, 3°, 2°, 1°, or less of each other.

As the beams of light 116, 118 enter the eye 102 at the corneal surface 104, a portion of the light is scattered by the corneal surface 104, and a portion of the light propagates through the cornea and into the eye 102. The beam of light 116 strikes the posterior wall of the capsular bag 106 at a first location 120, and a portion of the beam of light 116 is scattered by the posterior wall of the capsular bag 106. Similarly, the beam of light 118 strikes the posterior wall of the capsular bag 106 at a second location 122, and a portion of the second beam of light 118 is scattered by the posterior wall of the capsular bag 106.

The optics system 112 can collect a portion of the scattered light and can direct the collected light to a detector 124. In some embodiments, the optics system 112 is configured to focus the scattered light onto the detector 124. The optics system 112 can form an image on the detector 124. In some embodiments, the optics system 112 is designed such that the detector 124 and the posterior wall of the capsular bag 106 are located at conjugate planes. As will be discussed in more detail below, the optics system 112 can include various optical elements, such as mirrors, lenses, filters, apertures, and beam splitters. It should be understood that the optical axis 114 is not necessarily a straight line along the entire optical path within the ophthalmic measurement system 100 as it may be bent by various optical elements within the optics system 112. The detector 124 can comprise a charge-coupled device (CCD) or other type of photosensitive element. In some embodiments, the detector 124 includes a two-dimensional array of light-sensitive pixels configured to generate an electric signal that is descriptive of the light that strikes the pixels. For example, a CCD sensor measuring 16 mm by 16 mm and having a two-dimensional array of 500 by 500 pixels can be used, although other configurations are also possible.

The detector 124 can provide the electric signal to a processor 126. The processor 126 can be configured to process the data received from the detector 124 as described herein. In some embodiments, the processor 126 can be in electronic communication with a suitable memory 128 for storing accumulated data, instructions to be executed by the processor 126, parameters relating to the patient's eye 102, or other data. The processor 126 can also be in electronic communication with a user interface 142 to allow the user to input information regarding the patient's eye (e.g., aphakic or phakic), information regarding the distance to be measured, or other information.

Figure 2:
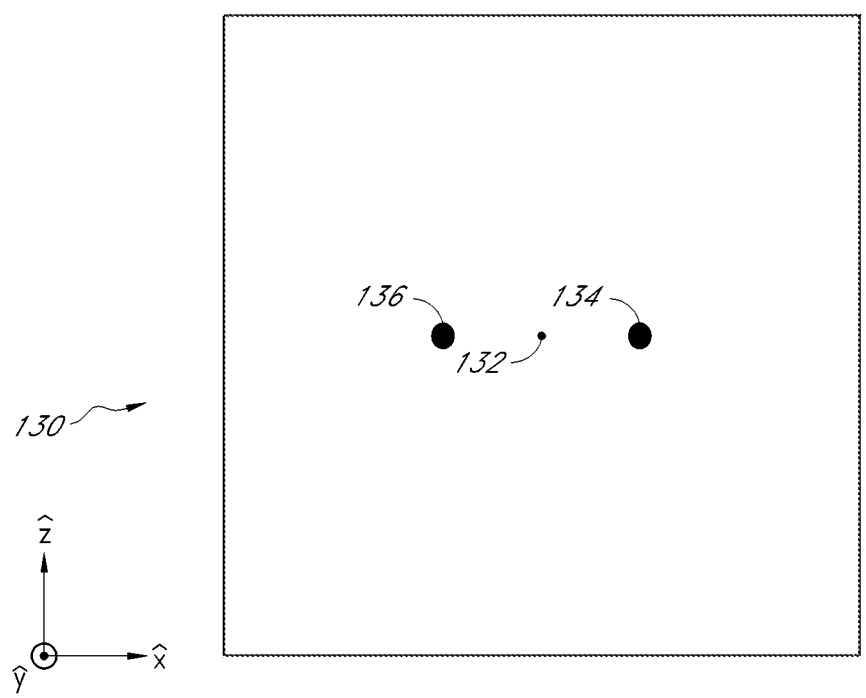
FIG. 2 is an example image produced by the ophthalmic measurement system of FIG. 1.

FIG. 2 shows an example image 130 that can be formed on the detector 124 during a measurement process. FIG. 2 includes a coordinate system similar to the coordinate system shown in FIG. 1. Although FIG. 2 shows the image 130 as being formed on the detector 124 in the x-z plane, the detector 124 can be oriented differently. The image 130 can include a center spot 132 corresponding to the light scattered at the corneal surface 104, a first target spot 134 corresponding to the light of the beam 116 scattered by the first location 120, and a second target spot 136 corresponding to the light of the beam 118 scattered by the second location 122. In some embodiments, the optics system 112 can be configured so as to provide a depth of field that is large enough so that the center spot 132 and both of the target spots 134, 136 are in focus so as to provide sharp focused spots on the detector 124. In some embodiments, the optics system can be configured so that one or more of the spots 132, 134, 136 is in focus and one or more of the spots 132, 134, 136 is appreciably out of focus. For example, in some embodiments, the center spot 132 can be appreciably out of focus while the target spots 134, 136 are in focus. The processor 126 can be configured to analyze the data received from the detector 124 and to determine therefrom a measurement of the distance $y_1$, for example. In some embodiments, this analysis may include locating the centroid of one or more of the spots 132, 134, 136 to be used in the measurement process and determining the distance between two or more of the spots 132, 134, 136.

The processor 126 can be configured to calculate the distance $y_1$ from the corneal surface 104 to the posterior wall of the capsular bag 106 based at least in part on the data received from the detector 124. The processor 126 can calculate the distance $x_1$ between the locations 120, 122 based on the positions of the target spots 134, 136 in the image 130. For example, the processor 126 can determine the number of pixels between the locations of the target spots 134, 136 and apply an algorithm that calculates the real-world distance between the locations 120, 122 represented by the target spots 134, 136. For example, the algorithm can account for any magnification provided by the optics system 112. In some embodiments, any refraction of the beams of light 116, 118 as they enter the eye and as they pass through the various optical transitions within the eye can be ignored, so that each of the beams of light 116, 118 can be treated as though it propagates from the corneal surface 104 to the posterior wall of the capsular bag 106 at the same non-zero angle $\theta$ with respect to the optical axis 114. In this embodiment, the distance $y_1$ can be calculated using equation (1) provided below.

$$y_1 = \frac{\frac{1}{2}x_1}{\tan(\theta)} \tag{1}$$

In some embodiments, the angle $\theta$ is not known, but the distance $x_2$ of separation between the lasers 108, 110 and the distance $y_2$ from the lasers to the corneal surface 104 are known. The distance $y_1$ can be calculated using equation (2) provided below.

$$y_1 = \frac{y_2 x_1}{x_2} \tag{2}$$

Alternatively, in some embodiments, the distances $y_2$ and $x_2$ can be used to first determine the angle $\theta$, and then equation (1) can be applied.

In some embodiments, the calculations for determining the distance $y_1$ can be adjusted to account for refraction of the beams of light as they enter the eye and/or as they propagate through the various refractive index transitions within the eye.

Although some embodiments discussed above describe the measurement of the posterior capsular bag depth in an aphakic eye, some embodiments can be used to measure other dimensions or spatial relationships of or in the patient's eye, such as, for example, the anterior chamber depth (ACD), which can be understood, for example, as the distance from the cornea to the anterior surface of the crystalline lens in a phakic eye. This distance can be between a selected position or portion of the cornea and a selected position or portion of the natural crystalline lens. The selected portion of the cornea can be, for example, the location on the corneal surface that intersects the visual axis of the eye. The selected portion of the crystalline lens can be, for example, all or a portion of its anterior surface of the lens, etc. The portion of the anterior surface can be, for example, the most anterior portion of the anterior surface, the position where the visual axis or the optical axis of the eye intersects the anterior surface, etc.

Figure 3:
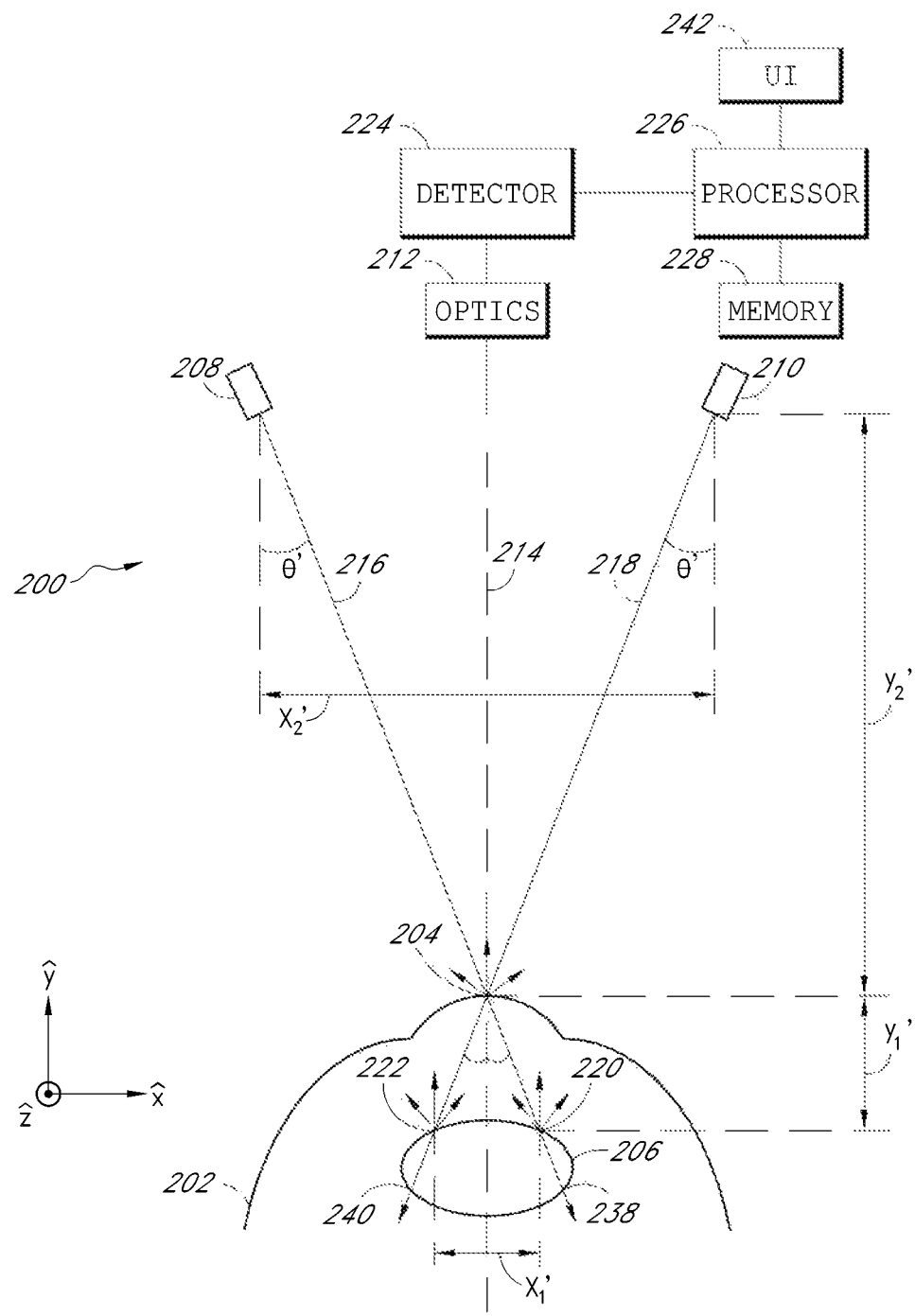
FIG. 3 schematically illustrates an embodiment of an ophthalmic measurement system for measuring dimensions of or in a patient's eye including, for example, the distance between the cornea and the anterior surface of the crystalline lens in a phakic eye.

FIG. 3 schematically shows an embodiment of an ophthalmic measurement system 200 for measuring dimensions of or in a patient's eye including, for example, the anterior chamber depth (ACD) in a phakic eye 202. The ophthalmic measurement system 200 can be similar in some ways to the ophthalmic measurement system 100 discussed above, some of the disclosure of which applies also the ophthalmic measurement system 200, though some differences are identified below. Accordingly, in some embodiments, for example, the ophthalmic measurement system 200 can be the same ophthalmic measurement system 100 used to measure the posterior capsular bag depth in an aphakic eye (as shown in FIG. 1), with or without modifications in configuration.

The ophthalmic measurement system 200 can include lasers 208, 210 configured to direct respective beams of light 216, 218 into the eye 202 of the patient through the corneal surface 204. The beams of light 216, 218 can therefore cross at the corneal surface 204 where a portion of the light from each of the beams 216, 218 is scattered by the corneal surface 204. The first beam of light 216 can propagate to a first location 220 on the anterior surface of the crystalline lens 206, which scatters a portion of light. Similarly, the second beam of light 218 can propagate to a second location 222 on the anterior surface of the crystalline lens 206, which scatters a portion of the light. A portion of the light scattered by the corneal surface 204 and the first and second locations 220, 222 can be collected by the optics system 212 and directed to the detector 224. In some embodiments, the optics system 212 or detector 224 can be especially configured for use with light reflected from the crystalline lens 206. For example, the optics system 212 can be configured to focus light differently than the optics system 112 used to measure the posterior capsular bag depth in an aphakic eye to accommodate for the different object distance. In some embodiments, the same optics system 112 and detector 124 can be used to measure the posterior capsular bag depth in an aphakic eye as well as the ACD in a phakic eye with or without the need for adjustments.

Figure 4:
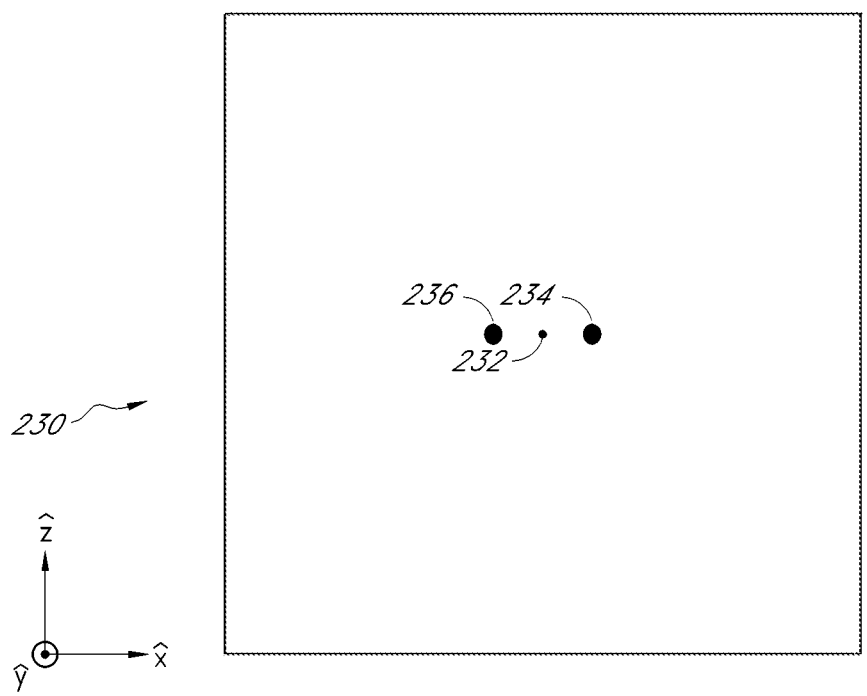
FIG. 4 is an example image produced by the ophthalmic measurement system of FIG. 3.

FIG. 4 shows an example image 230 formed on the detector 224 during a measurement process. FIG. 4 includes a coordinate system similar to the coordinate system shown in FIG. 2. The image 230 includes a center spot 232 corresponding to the light scattered at the corneal surface 204, a first target spot 234 corresponding to the light scattered by the first location 220 on the crystalline lens 206, and a second target spot 236 corresponding to the light scattered by the second location 222 on the crystalline lens 206. The processor 226 can be configured to calculate the distance $y_1'$ based on the locations of the spots 232, 234, 236 in a manner similar to that discussed above. It should be noted that the target spots 234, 236 may be slightly closer together than the target spots 134, 136, indicating that the distance $y_1'$ being measured by the image 230 is shorter than the distance $y_1$ being measured by the image 130.

Other distances within the patient's eye can similarly be measured. For example, the anterior aphakic capsular bag depth can be measured. This distance can be understood as, for example, the distance between the corneal surface and the anterior surface of the aphakic capsular bag. This measurement can be performed, for example, intra-operatively after the natural crystalline lens has been removed but before or after the globe and capsular bag have been inflated (e.g., with basic saline solution or visco-elastic material). This distance can be used, for example, separately from, or in conjunction with, the posterior aphakic capsular bag depth for calculating the ELP for an IOL. For example, in the case of an IOL that is inserted in the capsular bag, the estimated ELP can be selected to be some fraction of the way between these two distances. Other relationships relating these two distances to the estimated ELP of an IOL in the capsular bag are also possible and can be determined by, for example, regression analysis, as described herein. In addition, the anterior capsular bag depth measurement can be used for calculating the predicted position of a sulcus lens. For example, the estimated ELP of a sulcus lens could be related to the distance from the corneal surface to the anterior surface of the capsular bag by subtracting an empirically-derived constant from the measured distance. Other relationships relating this distance to the estimated ELP of a sulcus lens are also possible and can be determined by, for example, regression analysis, as described herein.

Also, the distance between the corneal surface 204 and the posterior wall of the capsular bag can be measured in the phakic eye 202 using light scattered by locations 238, 240 where the beams of light 216, 218 strike the posterior wall of the capsular bag. In some embodiments, the image 230 formed on the detector 224 can include more spots than those shown in FIG. 4. For example, the image may also include spots corresponding to light scattered by the locations 238, 240 on the posterior surface of the capsular bag, or by other structures within the eye. In some embodiments, the processor 226 can be configured to identify the spots relevant to the desired measurement, and ignore other spots in the image. For example, the processor 224 can disregard spots outside of a feasible range for the desired measurement or only consider spots that are sufficiently bright or sufficiently in focus. In some embodiments the optics system 212 can have a relatively short depth of field and be configured to focus only the spots in the feasible range for the desired measurement.

In some embodiments, the processor 226 can adjust the calculations, the optics system 212, or other components of the ophthalmic measurement system 200 based on information received via the user interface 242 regarding the patient's eye 202 or the measurement to be performed. For example, because the refractive power of an aphakic eye is different than the refractive power of the corresponding phakic eye, in some embodiments, the measurement system 200 can adjust the optics system 212 (e.g., by adjusting the position of lenses) to change the focal length of the camera depending on whether the eye being measured is phakic or aphakic. Such adjustments can be used to compensate for the varying extent to which the refractive power of a phakic or aphakic eye causes scattered light (e.g., from the anterior surface of the natural lens or from the posterior surface of the aphakic capsular bag) to be converged or diverged prior to exiting the eye and being collected by the optics system 112.

Many variations to the systems shown in FIGS. 1 and 3 are possible. For example, the lasers can be positioned at different longitudinal distances from the eye, or at different distances from the optical axis defined by the optics system. In some embodiments the lasers can be oriented at different angles with respect to the optical axis defined by the optics system. In some embodiments, the lasers can be positioned so that they cross at a location on the cornea that is not intersected by the visual axis of the eye or so that they cross at some other structure of the eye that is relevant to the desired measurement.

Figure 5:
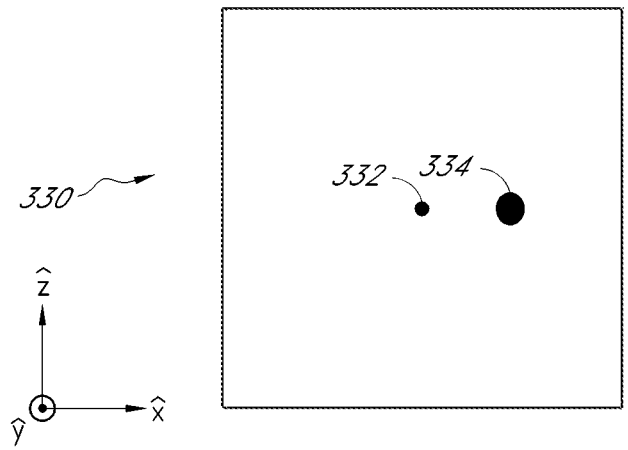
FIG. 5 is an example image produced by an ophthalmic measurement system similar to those of FIGS. 1 and 3 but with a single laser.

Although the embodiments described above disclose measurement systems using two lasers, other numbers of laser can be used. For example, in some embodiments, a single laser can be used. FIG. 5 shows an example image 330 formed on a detector in an ophthalmic measurement system similar to those of FIGS. 1 and 3 but with a single laser. FIG. 5 includes a coordinate system similar to the coordinate system described in connection with FIG. 2 above. The image 330 includes a center spot corresponding to light scattered at, for example, the corneal surface of the eye. The image also includes a target spot 334 corresponding to light scattered by, for example, the posterior wall of the capsular bag in an aphakic eye. The distance $y_1''$ (which can be the same distance as $y_1$ shown in FIG. 1) between the corneal surface and the posterior wall of the capsular bag may then be determined based in part on the locations of the spots 332, 334. For example, the distance $y_1''$ may be calculated from the x-direction component $x_1''$ of the distance between the corneal surface and the location on the capsular bag where the light is scattered (determined from the positions of the spots 332, 334) and the angle $\theta''$ of the incoming beam of light by using the equation (3) provided below:

$$y_i'' = \frac{x_1''}{\tan(\theta'')} \quad (3)$$

Figure 6:
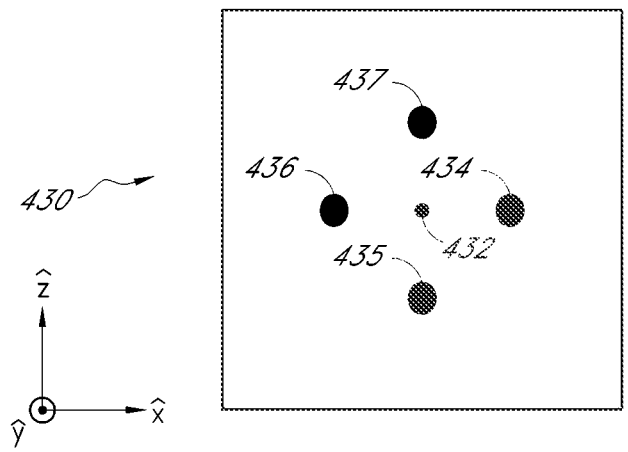
FIG. 6 is an example image produced by an ophthalmic measurement system similar to those of FIGS. 1 and 3 but with four lasers.

In some embodiments, four lasers can be positioned about optical axis and oriented so that the four beams of light intersect at the same location on the corneal surface. FIG. 6 shows an example image 430 formed on a detector of an ophthalmic measurement system similar to those of FIGS. 1 and 3 but with four lasers. FIG. 6 includes a coordinate system similar to the coordinate system described in connection with FIG. 2 above. The center spot corresponds to light scattered at the corneal surface of the eye. The four target spots 434, 435, 436, 437 correspond to the light from the respective four beams of light that is scattered at, for example, the posterior wall of the capsular bag. The distance between the corneal surface and the posterior wall of the capsular bag may then be determined based in part on the distance between the first target spot 434 and third target spot 436 and the distance between the second target spot 435 and the fourth target spot 437. The use of four lasers can provide information about the desired measurement along two axes, which in some embodiments may be orthogonal, as illustrated in FIG. 6. For example, if the distance between the first and third target spots 434, 436 is less than the distance between the second and fourth target spots 435, 437, that can indicate that the distance to be measured is shorter along the axis measured by the first and third target spots 434, 436 than along the axis measured by the second and fourth target spots 435, 437.

In some embodiments, additional lasers can be used to gather additional data regarding the surface being measured. For example, a grid of 8, 12, 16, or other number of lasers can be used to measure the distance from the corneal surface to the surface being measured at varying distances from the visual axis of the eye. Thus, the measuring system can be used to generate a more complete mapping of the surface of, for example, the posterior wall of the capsular bag, allowing for a more accurate prediction of the postoperative position of the IOL and thus a more accurate selection of IOL power. In some embodiments, the measurements conducted by the various sets of lasers in the grid can be performed at different times to prevent overlap of target spots on the detector. In some embodiments, the lasers can be movable (e.g., using gimbals and linear slides) and can be used to take measurements from multiple locations, so that a relatively thorough mapping of the surface can be obtained using a small number of lasers.

Figure 7A:
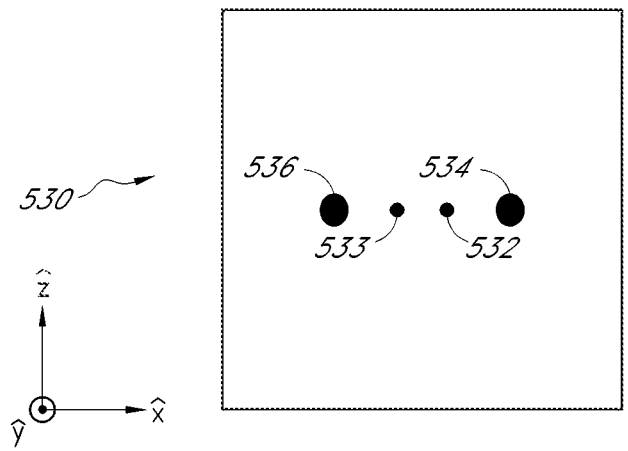
FIG. 7A is an example image produced by an ophthalmic measurement system similar to those of FIGS. 1 and 3 but when two lasers are oriented to produce laser light beams that do not intersect at the corneal surface of the eye.

In some embodiments, the processor (e.g., 126, 226) can determine whether the ophthalmic measurement system (e.g., 100, 200) is properly positioned at the desired location relative to the patient's eye based in part on the spots formed on the detector of the measurement system. FIG. 7A shows an example image 530 formed on the detector in an ophthalmic measurement system similar to those of FIGS. 1 and 3 but when the lasers (e.g., 108, 110, 208, 210) are oriented such that the beams of light (e.g., 116, 118, 216, 218) do not intersect at the corneal surface of the eye. FIG. 7A includes a coordinate system similar to the coordinate system described in connection with FIG. 2 above. The image 530 can be formed when the measurement system is positioned so that the longitudinal distance from the patient's eye (e.g., $y_2$, $y_2'$) is greater or less than the desired longitudinal distance, causing the beams of light emitted by the lasers to cross at a location in front of or behind the cornea of the eye. Because the beams of light cross before or after reaching the cornea, they strike the cornea at two different locations. The image 530 can include a first center spot 532 corresponding to light from the first beam of light that is scattered at a first location on the cornea of the eye. A second center spot 533 of the image 530 can correspond to the light from the second beam of light that is scattered at a second location on the cornea of the eye.

The image 530 can also include target spots 534, 536 corresponding to light scattered by the surface in the eye being measured, as discussed above. However, because the beams of light do not cross at the corneal surface of the eye, the distance between the target spots 534, 536 can produce inaccurate measurements if not properly compensated. Thus, in some embodiments, the processor can be configured to analyze the data provided by the detector and to only accept data for measurement purposes when the two center spots 532, 533 substantially overlap to form a single center spot, as shown, for example, in the example image 130 of FIG. 2. Thus, the measurement system can function to confirm that the positioning system (or the user) has properly positioned the measurement system at the desired working distance $y_2$, $y_2'$ prior to performing, or while performing, measurements of the eye. The formation of two center spots 532, 533 can also indicate that one or both of the lasers is improperly oriented or that some other malfunction has occurred.

In some embodiments, the measurement system (e.g., 100, 200) can provide positioning information to an automatic alignment system, or to the user. For example, when the apparatus is positioned at a working distance $y_2$, $y_2'$ that results in two distinct center spots 532, 533, the processor can cause the apparatus to move longitudinally with respect to the eye until a single center dot is formed. The processor can also be configured to align the apparatus with the apex of the eye by systematically moving the apparatus to locate the highest position on the eye that forms a single center spot on the measurement system detector.

In some embodiments, the measurement system (e.g., 100, 200) can determine whether its longitudinal position is greater than or less than the desired longitudinal distance from the eye. For example, if the center spots 532, 533 converge as the measurement system is brought closer to the eye or diverge as the measurement system is moved away from the eye, that can indicate that the lasers cross before reaching the corneal surface of the eye. Conversely, if the center spots 532, 533 diverge as the measurement system is brought closer to the eye or converge as the measurement system is moved away from the eye, that can indicate the that lasers cross after passing through the corneal surface of the eye. Alternatively, the lasers can have different sizes, use different frequencies of light, be time or frequency modulated, etc. so that the system can determine which of the center spots 532, 533 corresponds to which laser. For example, if the center spot 532 on the right side of the image 530 corresponds to the light emitted from the first laser and the center spot 533 on the left side of the image corresponds to the light emitted from the second laser, the system can determine that the lasers crossed before reaching the corneal surface. If the locations of the center spots 532, 533 are swapped, the system can determine that the lasers cross after passing through the corneal surface.

Figure 7B:
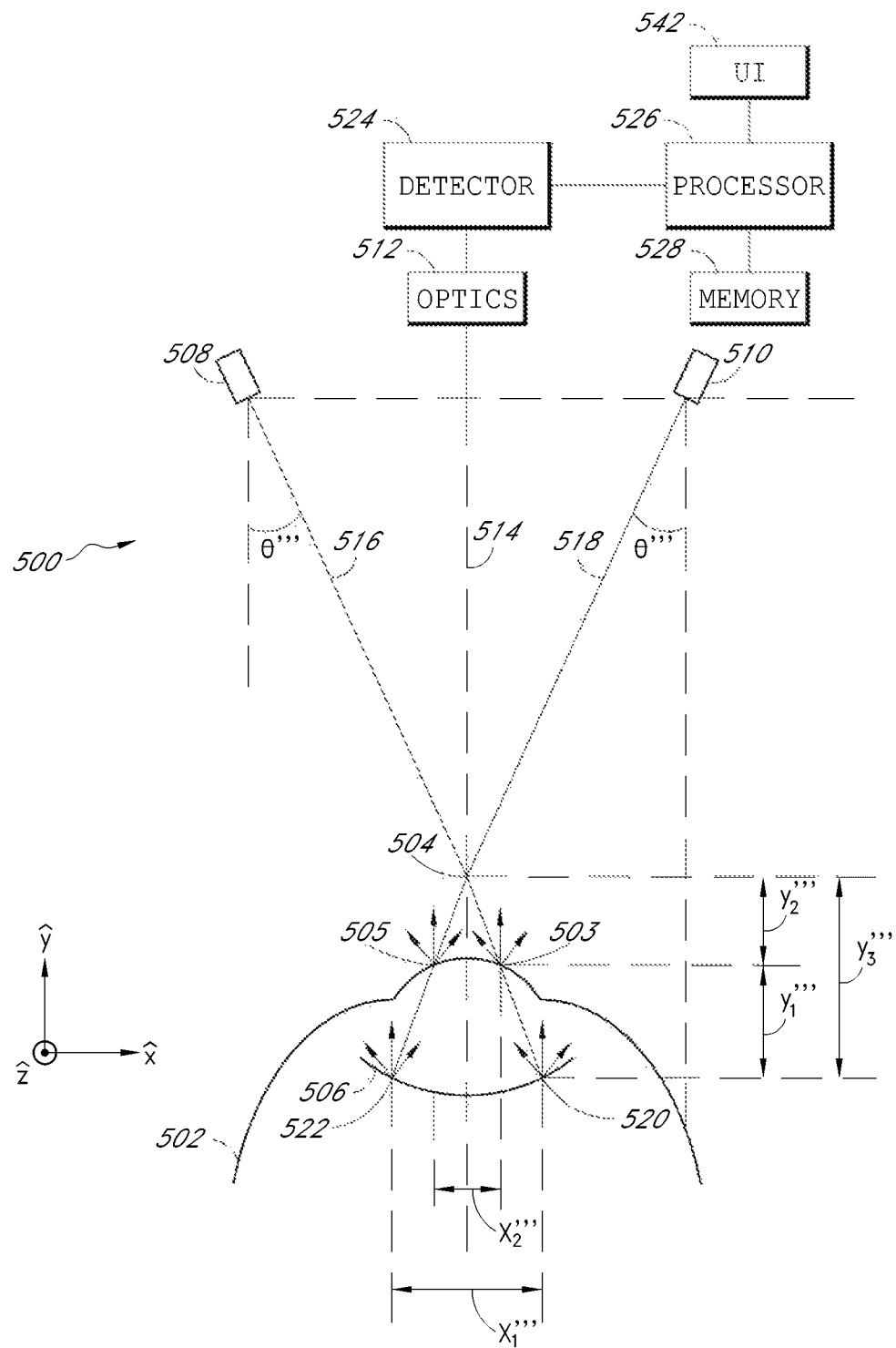
FIG. 7B schematically illustrates an embodiment of an ophthalmic measurement system for measuring dimensions of or in a patient's eye using two lasers that do not cross at the cornea of the eye.

FIG. 7B schematically illustrates an embodiment of an ophthalmic measurement system 500 for measuring dimensions of or in a patient's 502 eye using two lasers 508, 510 that do not cross at the cornea of the eye 502. The lasers 508, 510 emit beams of laser light 516, 518 that cross at a point 504 before the corneal surface of the eye 502. The beams of light 516, 518 strike the corneal surface of the eye at location 503 and location 505 respectively, propagate through the eye and strike the posterior surface of the aphakic capsular bag 506 at location 520 and location 522 respectively. At each of the locations 503, 505, 520, 522 a portion of the light is scattered by the cornea or capsular bag. A portion of the scattered light is collected by the optics 512 and directed to a detector 524. An image (such as the image 530 shown in FIG. 7A) is formed on the detector 524 having two center spots 532, 533 and two target spots 534, 536. The detector 534 can be electronically coupled to a processor 526, which can be coupled to a suitable memory 538 and a user interface 542.

The processor 526 can be configured to calculate the distance $y_1'''$ from the corneal surface to the posterior wall of the aphakic capsular bag 106 based in part on the data received from the detector 524. The processor 526 can be configured to calculate the distance $x_2'''$ between the locations 503, 505 where the laser beams 516, 518 intersect the cornea of the eye 502 based at least in part on the positions of the center spots 532, 533 in the image 530. Similarly, the processor 526 can be configured to calculate the distance $x_1'''$ between the locations 520, 522 on the posterior surface of the aphakic capsular bag 506 based at least in part on the positions of the target spots 534, 536. If the system 500 determines that the beams of laser light 516, 518 cross before reaching the corneal surface (for example, as discussed above), the distance $y_1'''$ can be defined using equation (4) provided below, wherein $y_3'''$ is the distance from the location 504 where the laser beams 515, 518 cross to the posterior wall of the aphakic capsular bag and $y_2'''$ is the distance from the location where the laser beams 516, 518 cross to the corneal surface of the eye 502.

$$y_1''' = y_3''' - y_2''' \qquad (4)$$

In some embodiments, the refraction of the beams of light 516, 518 as they enter the eye and propagate through the transitions within the eye can be ignored, so that the beams of light 516, 518 can be treated as though they propagate from the corneal surface to the posterior wall of the capsular bag 506 at the same non-zero angle $\theta'''$ with respect to the optical axis 514. In this embodiment, the distances $y_3'''$ and $y_2'''$ can be calculated using equations (5) and (6) provided below.

$$y_3''' = \frac{\frac{1}{2} x_1'''}{\tan(\theta)} \qquad (5)$$

$$y_2''' = \frac{\frac{1}{2} x_2'''}{\tan(\theta)} \qquad (6)$$

Equation (4) can then be rewritten as equation (7) provided below.

$$y_1''' = \frac{\frac{1}{2}(x_1''' - x_2''')}{\tan(\theta)} \qquad (7)$$

If the system 500 determines that the beams of laser light 516, 518 cross after passing through the corneal surface (as described above), the distance y1''' can be calculated using formula (8) provided below.

$$y_1''' = \frac{\frac{1}{2}(x_1''' + x_2''')}{\tan(\theta)} \qquad (8)$$

In addition, in some embodiments, an alignment system (e.g., 608 such as, for example, described herein) can also be used in determining the distances illustrated in FIG. 7B. For example, the alignment system can be used to determine $y_2'''$. As discussed above, in some embodiments, the calculations disclosed herein can be altered to account for refraction of the beams of light 516, 518 as they enter the eye 502 and/or refraction as the light propagates through the various transitions within the eye 502.

Figure 8:
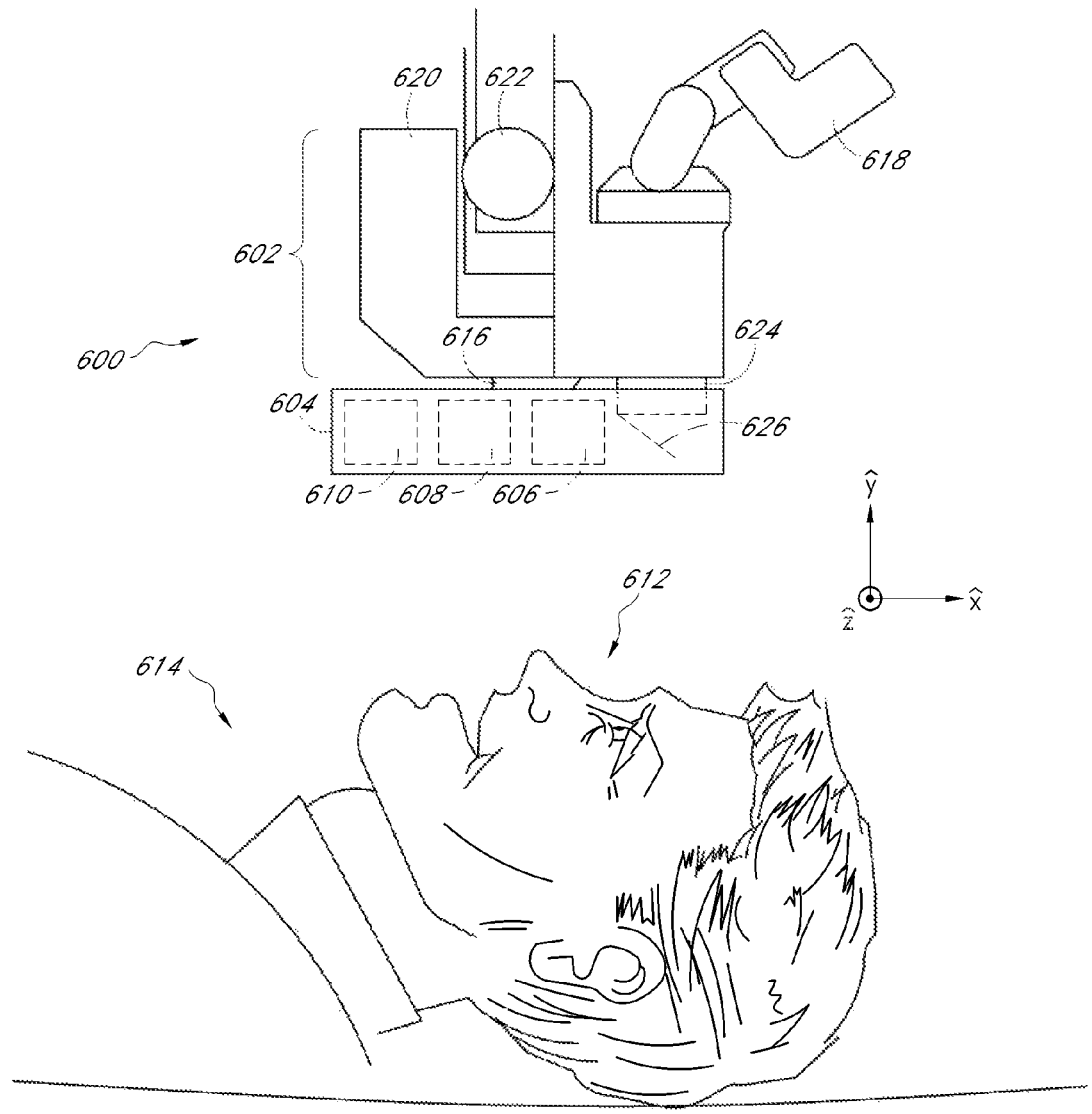
FIG. 8 schematically illustrates an embodiment of an ophthalmic apparatus that includes an alignment system and a measuring system mounted onto a surgical microscope.

FIG. 8 schematically shows an embodiment of an ophthalmic apparatus 600 that includes a measurement system 606, an alignment system 608, and a wavefront aberrometer 610 mounted onto a surgical microscope 602. The apparatus 600 can include an auxiliary module 604 attached to the surgical microscope 602. The auxiliary module 604 can include the measurement system 606, as described herein, the alignment system 608, and the wavefront aberrometer 610. The measurement system 606 can be used, for example, for measuring anterior and/or posterior capsular bag depth or ACD. The alignment system 608 can be used for transversely and longitudinally positioning the ophthalmic apparatus 600 at a desired location with respect to the patient's eye, as described herein. The wavefront aberrometer 610 can be used, for example, to perform intraoperative refractive power measurements of the patient's eye. For example, intraoperative measurements of the total refractive power of the patient's aphakic eye could be used in the calculation of IOL power in place of, or in addition to, preoperative corneal curvature and axial length measurements.

Although the measurement system 606, alignment system 608, and wavefront aberrometer 610 are illustrated as a single module 604, other configurations are possible. For example, the measurement system 606, alignment system 608, and wavefront aberrometer 610 can be arranged as two or three separate modules. In some embodiments, the measurement system 606 and wavefront aberrometer 610 can be rigidly mechanically and/or optically coupled together (as described in more detail below). The alignment system 608 can also be rigidly mechanically coupled to the measurement system 606. In some embodiments, the auxiliary module 604 can be removably attached to the surgical microscope 602 by one or more fasteners 616.

FIG. 8 illustrates an x-y-z coordinate system similar to the coordinate systems of FIGS. 1 and 3 for reference. Out of convenience the y-axis is aligned with the visual axis of the patient's eye, with the x- and z-axes being mutually orthogonal to the y-axis.

The alignment system 608 can be similar to the alignment system described in U.S. Patent Publication No. 2009/0103050, the entirety of which is hereby incorporated by reference herein. Other types of alignment systems can also be used. As discussed above, in some embodiments, the measurement system 606 can be used to provide positioning information, and the measurement system 606 can be used in conjunction with, or in place of, the alignment system 608 for positioning the apparatus 600 with respect to the eye 612 of the patient 614.

The wavefront aberrometer 610 can be, for example, a Talbot-Moire interferometer-type wavefront aberrometer, such as the wavefront aberrometer described in U.S. Pat. No. 6,736,510, the entirety of which is hereby incorporated by reference herein. It should be understood that other types of wavefront aberrometers may also be used. In some embodiments, the wavefront aberrometer 610 can be omitted, or a different ophthalmic instrument (e.g., a keratometer, corneal topographer, or Optical Coherence Tomography (OCT) system) can be used in addition to, or in its place of, the wavefront aberrometer 110, depending on the procedure to be performed.

The surgical microscope 602 can be any suitable style or configuration known in the art, or yet to be devised. The auxiliary module 604, and especially the fasteners 616, can be configured to securely attach to a variety of surgical microscopes. The surgical microscope 602 can include an eyepiece 618, which can be binocular or monocular, that allows a surgeon to view a region of the eye 612. The surgical microscope 602 can also include a light source 620 for illuminating the patient's eye 612, a focusing knob 622 for adjusting the focus of the surgical microscope 602, and an objective lens 624 for collecting light from the patient's eye 612. In some embodiments, the surgical microscope 602 is supported above the patient's eye by an adjustable boom.

In some embodiments, the measurement system 606 and/or the wavefront aberrometer 610 operates using light of non-visible wavelengths. Thus, the auxiliary module 604 can also include a wavelength selective mirror 626 that passes visible light to the objective lens 624 while reflecting light used by the measurement system 606 and/or the wavefront aberrometer 610, which may be, for example, in the near infrared range, to the measurement system 606 and/or the wavefront aberrometer 610 enclosed within the auxiliary module 604. It should be noted that the auxiliary module 604 can include additional optical components such as mirrors, lenses, beam splitters, filters, etc. for routing light to and among the components contained therein.

Figure 9:
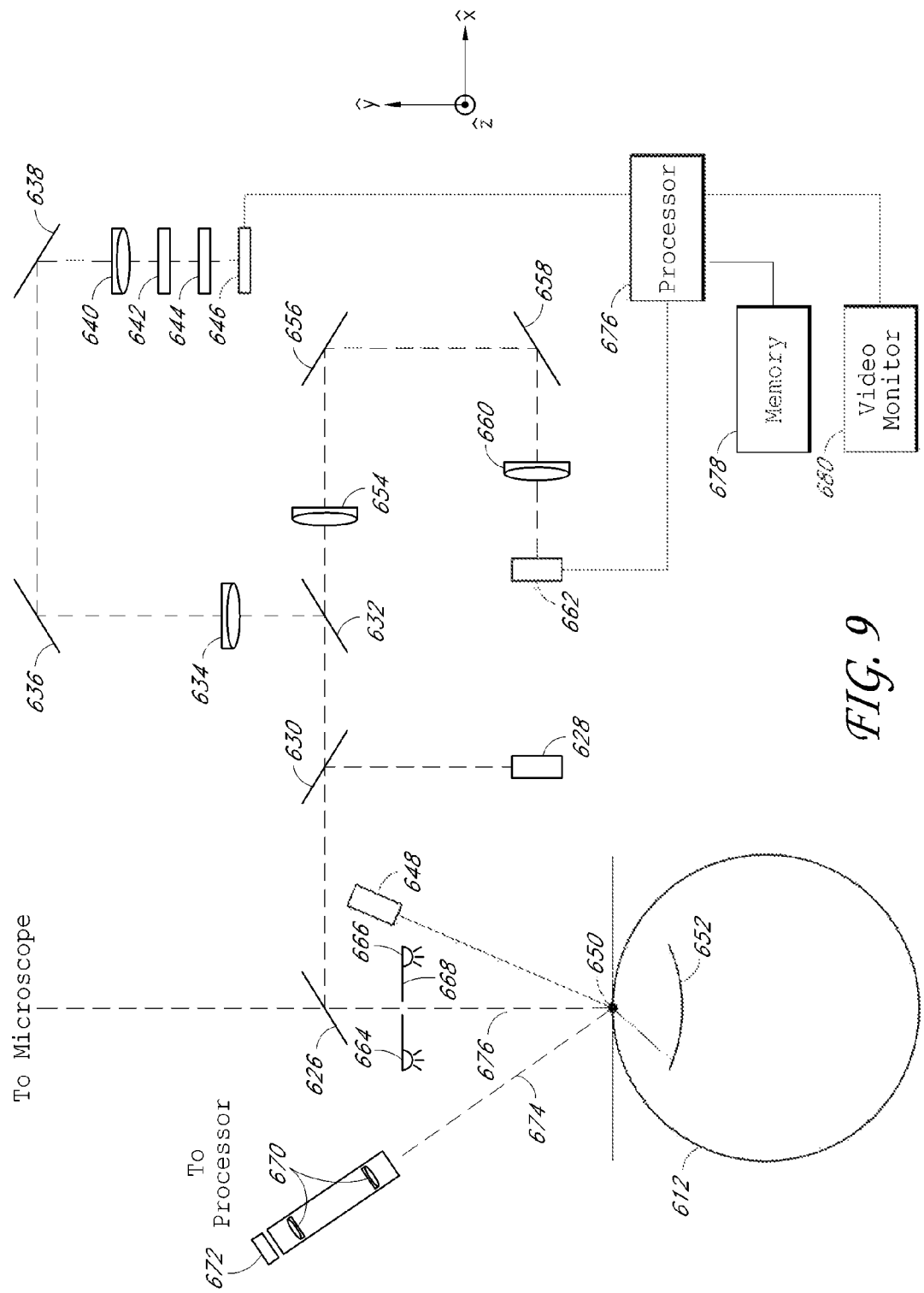
FIG. 9 schematically illustrates an embodiment of a wavefront aberrometer, a measurement system, and an alignment system for positioning the wavefront aberrometer and measurement system at a desired location relative to the patient's eye.

FIG. 9 schematically illustrates an embodiment of the measurement system 606, the alignment system 608, and the wavefront aberrometer 610. FIG. 9 illustrates an x-y-z coordinate system similar to the coordinate systems described above for reference. It should be noted that FIG. 9 is a schematic illustration, and the layout illustrated thereby does not necessarily indicate the actual locations and directions used in the apparatus 600. For example, the optical paths are illustrated as being located in the x-y plane for simplicity, though some of the optical paths can be directed at least in part in the z direction.

In the embodiment illustrated in FIG. 9, the wavefront aberrometer 610 includes a laser 628 that generates a thin beam of light having a planar wavefront which is directed by a first beam splitter 630 and a wavelength selective mirror 626 into the patient's eye 612. The laser light passes through the cornea and the pupil of the patient's eye and impinges on the retina. The laser light scatters from the retina and propagates back through the cornea of the eye 612 and toward the wavelength selective mirror 626.

Features of the eye 612, including the shape of the cornea, alter the planar wavefront of the scattered light, thus encoding information about the shape of the cornea and the refractive power of the eye in the altered wavefront. The altered wavefront is reflected by the wavelength selective mirror 626, passes through the first beam splitter 630, is reflected by a second beam splitter 632, passes through a first lens doublet 634, is re-directed by a first and second relay mirrors 636, 638, and passes through a second lens doublet 640. A pair of reticles, or gratings, 642, 644 is disposed between the second lens doublet 638 and the aberrometer detector 646. In some embodiments, the aberrometer detector 646 can be a charge-coupled device (CCD), although other detectors may also be used. The reticles 642, 644 can generate fringe patterns on the aberrometer detector 646 which are detected and used to determine the shape of the altered wavefront in, for example, the manner described in U.S. Pat. No. 6,736,510. The shape of the alternate wavefront can then be used to determine, for example, the spherical power, cylindrical power, and cylindrical axis of the patient's eye.

The measurement system 606 can include one or more lasers 648, only one of which is shown for simplicity, oriented to direct light into the eye as described above. In some embodiments, the lasers 648 can be rigidly attached to the outside of a housing associated with the auxiliary module 604, or inside the housing such that the laser light is directed through openings in the housing toward the patient's eye 612. In some embodiments, the lasers 648 can be attached having fixed angles.

When properly positioned, the laser light can enter the eye through the corneal surface 650 of the eye 612 and impinge upon the target surface 652 (e.g., the posterior wall of the capsular bag). Light can be scattered by both the corneal surface 650 and the target surface 652 within the eye 612. The scattered light is reflected by the wavelength selective mirror 626, passes through the first beam splitter 630 and the second beam splitter 632, passes through a third lens doublet 654, gets redirected by two mirrors 656, 658, and passes through a fourth lens doublet 660 toward a measurement system detector 662. As described above, the light received by the detector 662 can be used to determine the distance between the corneal surface 650 and the target surface 652 within the eye 612.

In some embodiments, an optical axis 676 of the apparatus is defined by the optics of the measurement system 606 and/or wavefront aberrometer 610. In some embodiments, the measurement system 606 and the wavefront aberrometer 610 are designed to operate at a common working distance so that they both can collect accurate data when the apparatus 600 is properly aligned at a desired transverse and longitudinal position.

In some embodiments, the lasers 648 of the measurement system 606 can use the same wavelength (e.g., 780 nm) of light as the laser 628 of the wavefront aberrometer 610. Thus the wavelength selective mirror 626 can be used to direct light from both the wavefront aberrometer 610 and the measurement system 606 toward the second beam splitter 632. In some embodiments, the measurements performed by the measurement system 606 and the wavefront aberrometer 610 can be performed at different times so that light from one system does not affect the measurements taken by the other. In some embodiments, the lasers 648 can use a different wavelength of light than the laser 628, so that measurements can be taken using the measurement system 606 at the same time that measurements are taken using the wavefront aberrometer 610, resulting in less waiting time during the surgical procedure. In such embodiments, wavelength selective mirror 626 can be configured to direct light of both wavelengths to the second beam splitter 632. In some embodiments, the apparatus 600 can use one or more wavelength selective mirrors to route light of one wavelength to the aberrometer detector 646 and light of another wavelength to the measurement system detector 662.

The alignment system 608 can include one or more light sources, such as light emitting diodes (LEDs) 664, 666. The LEDs 664, 666 can be positioned, for example, about the optical axis 676 of the apparatus and near the input window 668 of the wavefront aberrometer 610. In some embodiments, the LEDs 664, 666 use a different wavelength of light than the lasers 648, 628. For example, the LEDs can use light having a wavelength of 880 nm, although light of other wavelengths may also be used. The alignment system 608 also includes an alignment camera having alignment optics 670 and an alignment detector 672. The alignment optics 670 can define an alignment optical axis 674, which intersects the cornea of the eye 612. In some embodiments, the alignment optical axis 674 intersects the optical axis defined by the optics of the measurement system 606 and/or the wavefront aberrometer 610 at the corneal surface of the eye when the apparatus 600 is positioned at the desired location with respect to the patient's eye 612.

Light emitted from the LEDs 664, 666 propagates toward the cornea of the eye 612 and a portion of the light is reflected by the cornea generally along the alignment optical axis 674 so that it passes through the alignment optics 670 which creates an image of the LEDs 664, 666 on the alignment detector 672, which can be, for example, a CCD sensor. The positioning of the images of the LEDs 664, 666 will, in general, depend upon the spatial positioning of the apparatus 600 and the corneal curvature of the patient's eye. In some embodiments, a reference location can be defined on the detector 672 based on the corneal curvature of the patient's eye 612 and the desired position of the apparatus 600 with respect to the eye 612. From the position of the image of the LEDs 664, 666 relative to the reference location and the sharpness/focus of the image of the LEDs 664, 666, the alignment system 608 can provide alignment information for positioning the apparatus 600 at the desired location relative to the eye 612, as described in more detail in U.S. Patent Publication No. 2009/0103050. In some embodiments, the positioning system 608 can position the apparatus 600 to within 1 mm, 500 µm, 300 µm, or 150 µm of the desired location relative to the patient's eye 612.

The apparatus 600 can include a processor 676, which can be in electronic communication with the measurement system detector 662, the aberrometer detector 646, and the alignment detector 672. The processor can also be in electronic communication with a memory module 678 as discussed above, as well as a video monitor 680 or other display device for conveying information to the user. The processor 676 can receive and process data from the detectors 646, 662, 672 as described herein. In some embodiments, the processor 676 can use data from more than one of the detectors 656, 662, 672 to perform a function, such as produce positioning information. For example, as described above, in some embodiments, data from the measurement system 606 can be used in conjunction with the alignment system 608 to produce positioning information.

The apparatus 600 can include actuators (not shown) for automatically adjusting the position of the apparatus 600 based on the positioning information. The apparatus 600 can also include controls (not shown) that allow the user to adjust the position of the apparatus 600 according to the positioning information provided, for example, via the video monitor 680.

Figure 10:
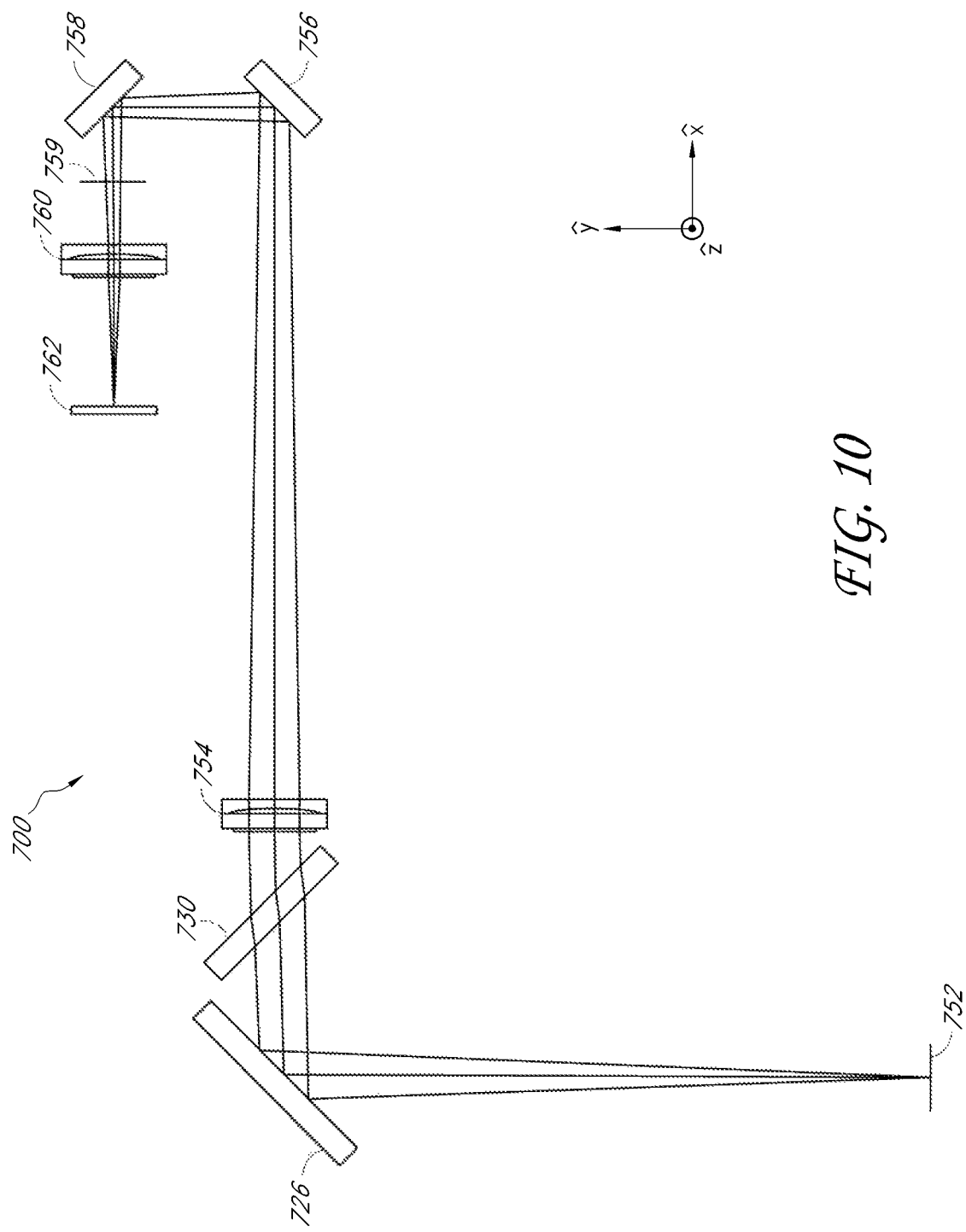
FIG. 10 schematically illustrates an embodiment of optics for use in an ophthalmic measurement system, the optics collecting light scattered by the patient's eye and directing the light to a detector.

In some embodiments, the ophthalmic measurement system 606 and the wavefront aberrometer 610 can use the same detector. FIG. 10 schematically illustrates an embodiment of the optics system 700 of an ophthalmic measurement system (e.g., 100, 200, 606) for collecting light scattered by the eye 752 from both the ophthalmic measurement system 606 and the wavefront aberrometer 610 and directing the light to a shared detector 762. A portion of the scattered light is reflected by a wavelength-selective mirror 726 (626 in FIG. 8) to a beam splitter 730, which transmits a portion of the scattered light toward a first lens 754. The wavelength-selective mirror 726 can be used, for example as described herein, to transmit visible light to a surgical microscope while reflecting infrared light used by the measurement system 606 and wavefront aberrometer 610. The beam splitter 730 can be used, for example as described herein, to direct a portion of a beam of laser light from a laser (628 in FIG. 8) to the eye 752 for use by the wave front aberrometer 610.

The first lens 754 can be a lens doublet and can operate with optical power on the scattered light. For example, the lens 754 can act to converge the scattered light, and direct it to a first mirror 756, which reflects the light to a second mirror 758. The second mirror 758 can direct the scattered light through a spatial aperture 759 to a second lens 760, which can be a doublet lens and can operate with optical power on the scattered light. For example the lens 760 can act to further converge the scattered light to form a real image on the detector 762. It should be understood that many other choices for the optical components in the optics system 700 and the layout thereof can also be used. The optical system 700 can include a pair of gratings (not shown in FIG. 10) positioned between the lens 760 and the shared detector 762.

In some embodiments, the positions of the optical elements of the optical system 700 are fixed. In some embodiments, some of the optical elements of the system 700 can be movable. For example, the lens 760 and/or the lens 754 can be movable so as to adjust the effective focal length of the optics system 700 depending on the measurement being taken (e.g., posterior or anterior aphakic capsular bag depth or ACD), the characteristics of the eye being measured (e.g., phakic or aphakic), whether the measurement system 606 or the wavefront aberrometer 610 is being used, etc. Thus, the optics system 700 can be configured to form a sharp, focused image on the detector 762 for a variety of applications. In some embodiments, the gratings can be movable so that they can be placed in the optical path when the wavefront aberrometer is in use and removed from the optical path when the measurement system 606 is in use. In some embodiments, the gratings can remain in the optical path when the measurement system 606 is in use.

FIG. 10 contains an x-y-z coordinate system in which the y-axis is aligned with the visual axis of the eye and the x- and z-axes are mutually orthogonal to the y-axis. Other coordinate systems can be used, and the optical elements illustrated in FIG. 10 can be oriented in directions other than that shown in FIG. 10.

Figure 11:
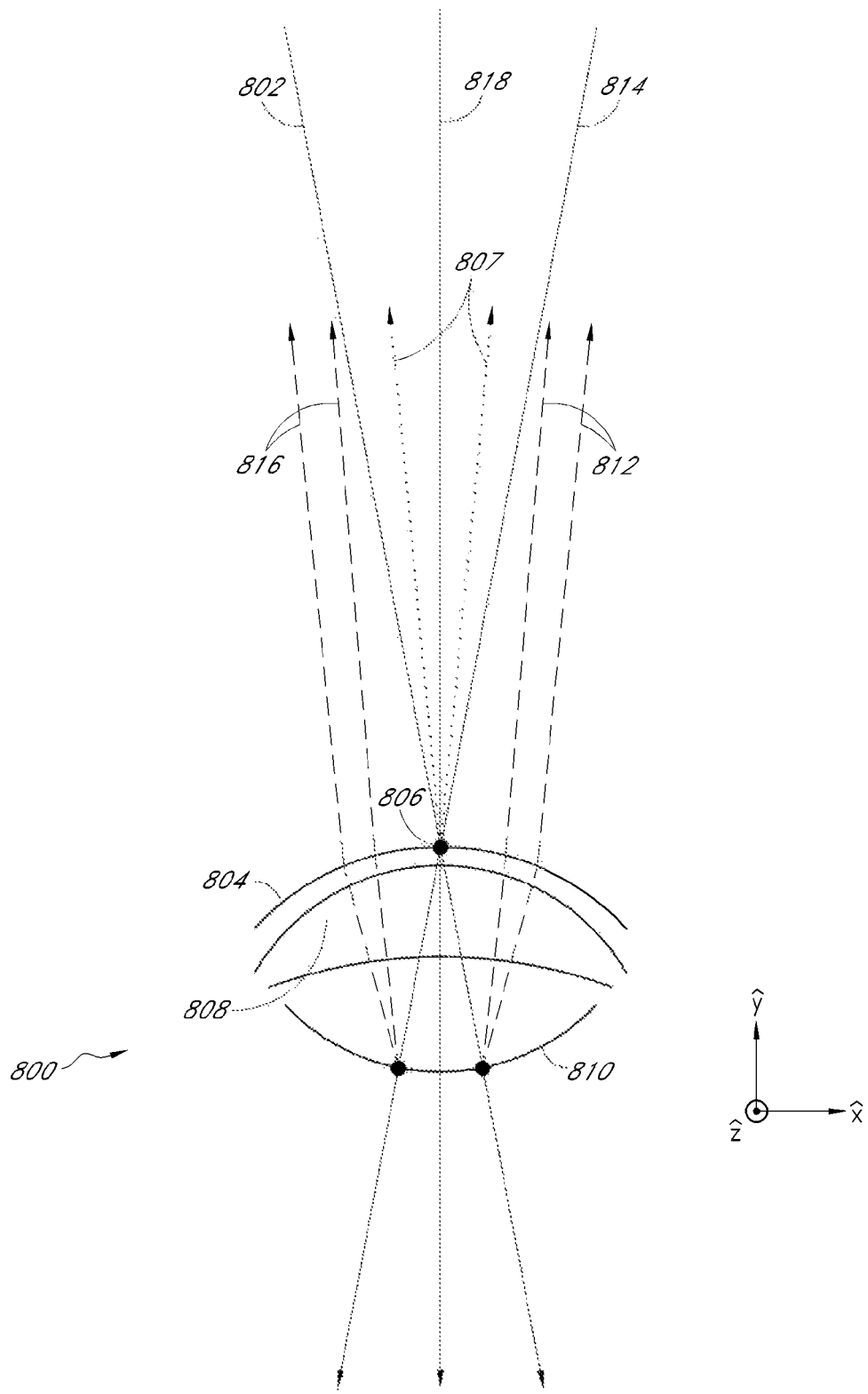
FIG. 11 schematically illustrates light from the ophthalmic apparatus of FIG. 8 interacting with an optical model of a patient's eye during a measurement process.

FIG. 11 schematically illustrates light from the ophthalmic apparatus of FIG. 8 interacting with an optical model of a patient's eye 800 during a measurement process. FIG. 11 contains an x-y-z coordinate system in which the y-axis is aligned with the visual axis of the eye and the x- and z-axes are mutually orthogonal to the y-axis. Other coordinate systems can be used.

A first beam of laser light 802 contacts the cornea 804 of the eye 800 at the corneal surface 806. A portion of the light 802 is scattered at the corneal surface, shown in FIG. 11 as dotted lines 807. The first beam of laser light 802 passes through various structures of the eye, including the cornea 804, the aqueous humor 808, etc. The first beam of laser light 802 can be refracted as it enters the eye 800 and propagates through the various structures of the eye. The first beam of laser light 802 eventually impinges on the posterior wall of the capsular bag 810, where part of the light 802 is scattered (shown as dashed lines 812) and part of the light 802 passes through the capsular bag and propagates further into the eye 800. The scattered light 812 can be refracted by the various transitions within the eye and can also be refracted as it exits the eye 800. As will be understood by those of skill in the art, the ray trace shown in FIG. 11 is a simplified ray trace, showing relatively few rays of light for simplicity. For example, the beams of laser light (e.g., 802) are shown as a single ray, when during actual operation the beams of laser light can have a perceptible thickness.

A second beam of laser light 814 can enter the eye 800 through the corneal surface 806. A portion of the second beam of laser light 814 is also scattered by the corneal surface 806 (the scattered light is shown in FIG. 11 by dotted lines 807). The second beam of laser light 814 can be refracted similarly to the first beam of light 802 discussed above, as it enters the eye 800 and propagates to the posterior wall of the capsular bag 810. A portion of the second beam of light 814 can be scattered by the capsular bag 810 (the scattered light is shown in FIG. 11 as dashed lines 816). The scattered light 816 can be refracted as it propagates through the transitions within the eye 800 and as it exits the eye 800. The scattered light 807, 812, 816 can be directed to a detector and used to determine the distance from the corneal surface 806 to the posterior wall of the capsular bag 810, as discussed herein.

A third beam of laser light 818 can be directed into the eye 800 through the corneal surface 806 so that it propagates to the retina (not shown) and is scattered by the retina. In some embodiments, the third beam of laser light 818 correspond to the probe beam of the wavefront aberrometer 610, as described herein. The scattered light from the retina can be used by the wavefront aberrometer 610 to measure the optical power of the eye.

Figure 12:
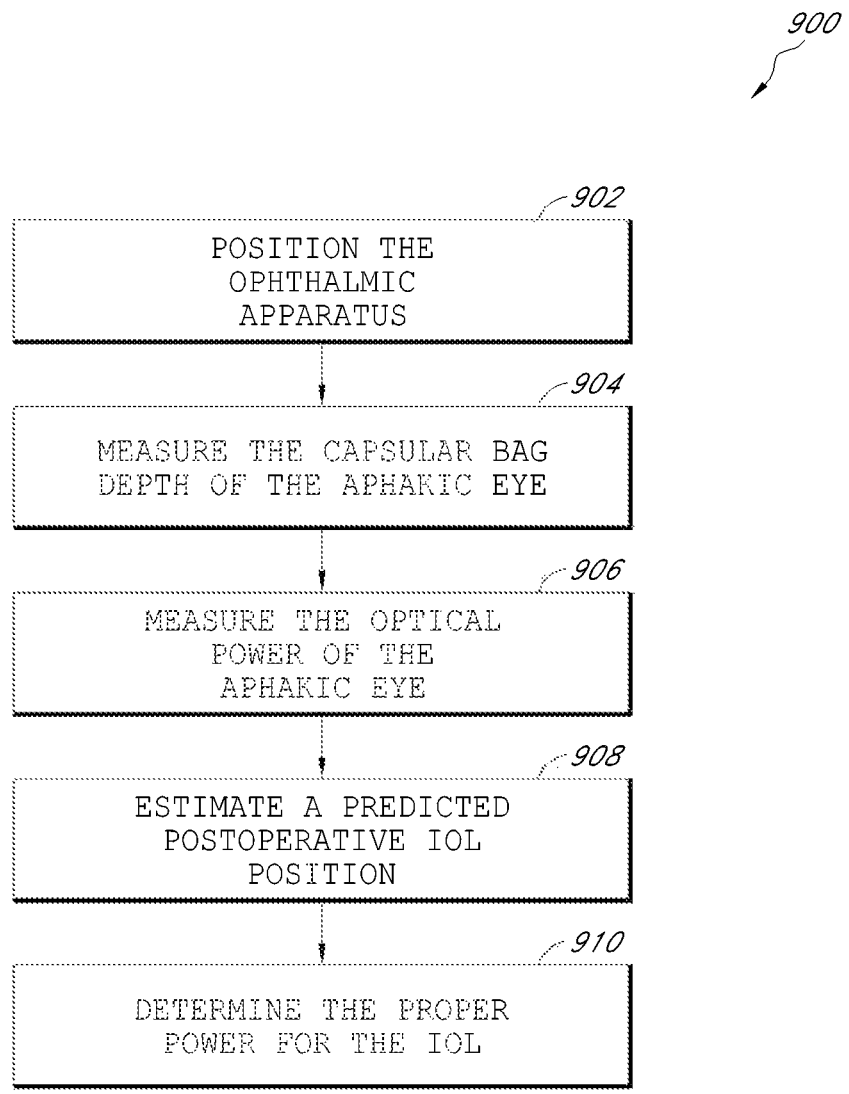
FIG. 12 is a flowchart showing an example embodiment of a method for determining the power for an intraocular lens (IOL) for insertion in a given patient's eye.

FIG. 12 is a flowchart showing an embodiment of a method 900 for determining appropriate optical power for an IOL to be implanted into a patient's eye as part of a cataract surgery. At block 902, the user can position the ophthalmic apparatus 600 at a predetermined desired position over the eye of the patient. In some embodiments, the desired position can place the apparatus laterally so that an optical axis of the measurement system substantially aligns with the visual axis of the eye, and longitudinally so that the lasers of the measurement system intersect at the corneal surface of the eye. In some embodiments, the user can use the surgical microscope to coarsely position the apparatus 600. During some applications, it may be desirable to fine tune the position of the apparatus 600 using the alignment system 608, as described herein. In some embodiments, the alignment system 608 can be used in conjunction with the wavefront aberrometer 610 and/or the spatial measurement system (e.g., 100, 200, 606) to generate positioning information. The positioning of the apparatus may be performed automatically using a processor and actuators, or manual using controls provided to the user. It should be noted that although the method 900 described in relation to the apparatus 600, a different ophthalmic apparatus can be used. For example, an ultrasound or optical coherence tomography measurement device can be used. In some embodiments, the ultrasound or optical coherence tomography device can be mounted onto the surgical microscope or onto the aberrometer, but space restrictions may limit the type of measurement device mounted thereto. The apparatus may be positioned differently with respect to the patient's eye depending on the type measuring device used.

At block 904, the apparatus 600 can be used to measure at least one intraoperative characteristic of the eye, such as the posterior capsular bag depth of the aphakic eye. In some embodiments, the additional step of removing the natural crystalline lens from the eye can be performed beforehand, converting the eye into an aphakic eye. In addition, the globe and capsular bag can be inflated (e.g., with basic saline solution or a visco-elastic material) after the natural crystalline lens is removed. In some embodiments, an ophthalmic measurement system (e.g., 100, 200, 606) as described herein can be used to measure the posterior capsular bag depth. Light from one or more lasers (e.g., 108, 110, 208, 210) can be directed into the eye through the corneal surface so that light from the lasers is scattered by the corneal surface and also scattered by the capsular bag within the eye. The scattered light can be collected and directed to a detector where spots are formed corresponding to the locations from which the light was scattered. A processor can be configured to determine the posterior capsular bag depth of the aphakic eye based at least in part on the positions of the spots formed on the detector, as described herein. In some embodiments, the posterior capsular bag depth can be measured using ultrasound technology or optical coherence tomography. Other intraoperative characteristics of the eye can be measured in addition to, or instead of, the posterior aphakic capsular bag depth. For example, anterior aphakic capsular bag depth can be measured. This distance can be used, for example, to predict the postoperative position of an IOL to be placed anterior of the capsular bag (e.g., a sulcus lens) rather than inside the capsular bag itself. This distance can also be used instead of, or in conjunction with, the posterior aphakic capsular bag depth to predict the postoperative position of an IOL in the capsular bag. Other intraoperative characteristics of the eye can also be measured.

At block 906, the apparatus 600 can be used to measure the optical power of the aphakic eye. For example, a wavefront aberrometer 610 can be used to measure the optical power of the aphakic eye, as described herein. In other embodiments, the optical power of the aphakic eye can be determined by other methods. For example, the optical power of the aphakic eye can be estimated from the curvature of the cornea and the axial length of the eye.

At block 908, a predicted post operative IOL position can be calculated based at least in part on the measured at least one intraoperative characteristic of the eye (e.g., the aphakic capsular bag depth of the eye). In some embodiments, the predicted post operative position of the IOL can be determined based on the measured posterior aphakic capsular bag depth without the use of additional measurements of the eye. For example the ELP for the IOL can be determined by subtracting a constant from the measured posterior aphakic capsular bag depth. In some embodiments, the measured optical power of the aphakic eye or other factors can also be considered to predict the post operative IOL position, such as the curvature of the cornea, the axial length of the eye, etc. As will be understood by those of skill in the art, the correlation between aphakic capsular bag depth and the postoperative IOL position can be established by measuring the actual postoperative IOL position for patients for which the aphakic capsular bag depth was measured, and, after a sufficient sampling, a statistical regression algorithm or the like can be used to generate a relationship between the aphakic capsular bag depth and postoperative IOL position. In some embodiments, the postoperative position of an IOL inside the capsular bag can be predicted. The postoperative position of an IOL at other locations (e.g., for a sulcus lens) can also be predicted.

At block 910, the power for the IOL to be implanted into the patient's eye can be calculated using, at least in part, the predicted postoperative IOL position. Other factors can also be considered, such as the optical power of the aphakic eye, the axial length of the eye, etc. By accurately estimating the postoperative IOL position, an appropriate power for the IOL can be selected more accurately, yielding superior surgical results that can be more effective at restoring a patient's eye to an emmetropic condition.

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps may be altered, added, removed, or rearranged. Additionally, processing steps may be added, removed, or reordered. While certain embodiments have been explicitly described, other embodiments will also be apparent to those of ordinary skill in the art based on this disclosure.

The foregoing disclosure has partitioned devices and systems into multiple components or modules for ease of explanation. It is to be understood, however, that one or more components or modules may operate as a single unit. Conversely, a single component or module may comprise one or more sub-components or some-modules. Further, the communication between components or modules may occur in a variety of ways, such as hardware implementations (e.g., over a network or internal bus), software implementations, or a combination of hardware and software. Such communications can use a variety of signals, protocols, system architectures, and standards such as, for example, radio signals and networks. Modules disclosed herein can include hardware, software, firmware, electronic, and optical elements.

Some aspects of the systems and methods described herein can advantageously be implemented using, for example, computer software, hardware, firmware, or any combination of software, hardware, and firmware. Software modules can comprise computer executable code for performing the functions described herein. In some embodiments, computer-executable code is executed by one or more general purpose computers. However, a skilled artisan will appreciate, in light of this disclosure, that any module that can be implemented using software to be executed on a general purpose computer can also be implemented using a different combination of hardware, software, or firmware. For example, such a module can be implemented completely in hardware using a combination of integrated circuits. Alternatively or additionally, such a module can be implemented completely or partially using specialized computers designed to perform the particular functions described herein rather than by general purpose computers.

A skilled artisan will also appreciate, in light of this disclosure, that multiple distributed computing devices can be substituted for any one computing device illustrated herein. In such distributed embodiments, the functions of the one computing device are distributed (e.g., over a network) such that some functions are performed on each of the distributed computing devices.

While certain embodiments have been explicitly described, other embodiments will become apparent to those of ordinary skill in the art based on this disclosure. Therefore, the scope of the invention is intended to be defined by reference to the claims and not simply with regard to the explicitly described embodiments.

What is claimed is:

1. A method of determining the optical power for an intraocular lens to be implanted into an eye, the method comprising:
   measuring an intraoperative characteristic of the eye with at least one laser beam, the intraoperative characteristic comprising the distance between selected portions of a cornea of the eye and a capsular bag of the eye; and
   determining the optical power for the intraocular lens based at least in part on the measured intraoperative characteristic.

2. The method of claim 1, wherein the eye is aphakic.

3. The method of claim 2, wherein the intraoperative characteristic comprises the distance from the cornea of the eye to the posterior wall of the capsular bag in the aphakic eye.

4. The method of claim 3, wherein determining the optical power for the intraocular lens comprises:
   determining a predicted postoperative lens position of the intraocular lens based at least in part on the measured distance from the cornea to the posterior wall of the capsular bag; and
   calculating the optical power for the intraocular lens based at least in part on the predicted postoperative lens position.

5. The method of claim 1, further comprising:
   measuring the refractive power of the aphakic eye; and
   determining the optical power for the intraocular lens based at least in part on the refractive power of the aphakic eye.

6. A method of determining the optical power for an intraocular lens to be implanted into an eye, the method comprising:
   measuring an intraoperative characteristic of the eye, the intraoperative characteristic comprising the distance between a selected first portion of a cornea of the eye and a portion of an aphakic capsular bag within the eye; and
   determining the optical power for the intraocular lens based at least in part on the measured intraoperative characteristic.

7. The method of claim 6, wherein the intraoperative characteristic comprises the distance from the cornea of the eye to the posterior wall of the capsular bag in the aphakic eye.

8. The method of claim 6, wherein determining the optical power for the intraocular lens comprises:
   determining a predicted postoperative lens position of the intraocular lens based at least in part on the measured intraoperative characteristic; and
   calculating the optical power for the intraocular lens based at least in part on the predicted postoperative lens position.

9. The method of claim 6, further comprising:
   measuring the refractive power of the aphakic eye; and
   determining the optical power for the intraocular lens based at least in part on the refractive power of the aphakic eye.

10. An ophthalmic apparatus, comprising:
    a first laser configured to direct a first beam of light into an eye of a patient at a first non-zero angle with respect to an optical axis of the apparatus, such that the first beam of light propagates to a target area within the eye, and such that a portion of the first beam of light is scattered by the target area;
    imaging optics positioned to receive light scattered by the target area, the imaging optics defining the optical axis of the apparatus;
    a photosensitive element, wherein the imaging optics direct the light scattered from the target area to the photosensitive element; and
    a processor configured to intraoperatively determine a distance between the cornea of the eye and the target area within the eye based at least in part on the light received by the photosensitive element,
    wherein the target area comprises a portion of the aphakic capsular bag of the eye, and wherein the processor is further configured to determine, based on the distance between the cornea and the target area, an estimate of the position of an intraocular lens that is to be implanted into the eye.

11. The ophthalmic apparatus of claim 10, wherein the processor is configured to calculate the distance between a corneal surface of the eye and the target area within the eye.

12. The ophthalmic apparatus of claim 10, wherein the processor is configured to calculate the distance between the location on the cornea where the optical axis of the apparatus intersects the cornea and the target area within the eye.

13. The ophthalmic apparatus of claim 10, wherein the target area comprises a posterior wall or anterior surface of the capsular bag.

14. The ophthalmic apparatus of claim 10, wherein the optical axis of the apparatus intersects the corneal surface of the eye at substantially the same location as the visual axis of the eye, and wherein the optical axis of the apparatus is substantially collinear with the visual axis of the eye.

15. The ophthalmic apparatus of claim 10, further comprising:

a second laser oriented to direct a second beam of light into the eye at a second non-zero angle with respect to the optical axis of the apparatus, such that the second beam of light propagates to the target area within the eye, and such that a portion of the second beam of light is scattered by the target area;

wherein the portion of the first beam of light scattered by the target area forms a first target spot on the photosensitive element and the portion of the second beam of light scattered by the target area forms a second target spot on the photosensitive element; and wherein the processor is configured to calculate the distance between the cornea of the eye and the target area within the eye based at least in part on the positions of the first and second target spots.

16. The ophthalmic apparatus of claim 15, wherein the processor is configured to calculate the distance between the cornea of the eye and the target area within the eye based at least on the distance between the first and second spots.

17. The ophthalmic apparatus of claim 15, wherein the first and second lasers are oriented so that the first and second beams of light both enter the eye substantially at the location on the corneal surface of the eye, such that a portion of the first and second beams of light is scattered at the corneal surface and received by the photosensitive element, wherein the portion of the first beam of light scattered by the corneal surface forms a first center spot on the photosensitive element and the portion of the second beam of light scattered by the corneal surface forms a second center spot on the photosensitive element, and wherein the first and second center spots substantially overlap when the apparatus is positioned at a predetermined position.

18. The ophthalmic apparatus of claim 17, wherein the first and second lasers are positioned on opposite sides of the optical axis of the apparatus, wherein the first and second lasers are spaced substantially equidistant from the optical axis of the apparatus, and wherein the first and second non-zero angles have substantially equal values and extend in substantially opposite directions from the optical axis of the apparatus.

19. The ophthalmic apparatus of claim 10, wherein the first laser is oriented so that the first beam of light enters the eye through the corneal surface of the eye, such that a portion of the first beam of light is scattered at the corneal surface and received by the imaging optics, the portion of the first beam of light scattered at the corneal surface forming a reference spot on the photosensitive element, the portion of the first beam of light scattered by the target area forming a target spot on the photosensitive element, and wherein the processor is configured to calculate the distance between the cornea of the eye and the target area within the eye based at least in part on the position of the target spot relative to the reference spot.

20. The ophthalmic apparatus of claim 10, further comprising an alignment system for positioning the apparatus at a predetermined position relative to the eye.

21. The ophthalmic apparatus of claim 20, wherein the first beam of light enters the eye at the center of the corneal surface of the eye.

22. The ophthalmic apparatus of claim 10, wherein the non-zero angle is between about 10 degrees to about 20 degrees.

23. The ophthalmic apparatus of claim 10, further comprising a surgical microscope.

24. The ophthalmic apparatus of claim 10, further comprising a wavefront aberrometer.

* * * * *